(12) United States Patent
Jones et al.

(10) Patent No.: US 8,742,368 B2
(45) Date of Patent: Jun. 3, 2014

(54) DEVICE AND METHOD FOR MEASURING SCATTERING OF RADIATION

(75) Inventors: Robert Jones, Cambridge (GB); Roger Fane Sewell, Cambridge (GB); Paul D. Ryder, Cambridge (GB); Matthew J. Hayes, Cambridge (GB); Edwin C. Carter, Cambridge (GB)

(73) Assignee: Cambridge Consultants Limited, Cambridge (GB)

( * ) Notice: Subject to any disclaimer, the term of this patent is extended or adjusted under 35 U.S.C. 154(b) by 856 days.

(21) Appl. No.: 12/865,432

(22) PCT Filed: Feb. 2, 2009

(86) PCT No.: PCT/GB2009/000259
§ 371 (c)(1),
(2), (4) Date: Dec. 15, 2011

(87) PCT Pub. No.: WO2009/095679
PCT Pub. Date: Aug. 6, 2009

(65) Prior Publication Data
US 2012/0080611 A1    Apr. 5, 2012

(30) Foreign Application Priority Data

Feb. 1, 2008  (GB) .................................. 0801850.9
Feb. 1, 2008  (GB) .................................. 0801871.5
Jul. 25, 2008  (GB) .................................. 0813679.8

(51) Int. Cl.
*F21V 9/16*  (2006.01)
(52) U.S. Cl.
USPC ....................................................... 250/458.1
(58) Field of Classification Search
USPC .......................................... 250/458.1, 459.1
See application file for complete search history.

(56) References Cited

U.S. PATENT DOCUMENTS

| 3,822,095 A | 7/1974 | Hirschfeld |
| 5,352,901 A | 10/1994 | Poorman |

(Continued)

FOREIGN PATENT DOCUMENTS

| EP | 0 522 548 A1 | 1/1993 |
| EP | 1 063 512 A2 | 12/2000 |

(Continued)

*Primary Examiner* — David Porta
*Assistant Examiner* — Edwin Gunberg
(74) *Attorney, Agent, or Firm* — Fogg & Powers LLC

(57) ABSTRACT

A photometric device for investigating a sample, comprises an array of radiation sources that are spaced apart from one another, and which are operable to generate radiation that differs from that generated by the other radiation sources in the array. The device includes a lens arrangement for focusing the radiation at a region of space where a sample may be located for example by means of a sample holder, and at least one detector for receiving radiation from the region of space. Preferably, a number of detectors are employed that are spaced apart from one another, and especially about an axis of the device, so that one radiation detector can detect radiation transmitted by the sample and the other detectors can detect radiation scattered by it. The radiation sources may be time division multiplexed so that in each time slot the detectors receive radiation originating from each radiation source. In an alternative embodiment, the radiation from the region of space may be transmitted to the sample via a beam homogeniser, for example an optical waveguide in the form of an optical fibre, which may be used to reduce or remove speckle where laser diodes are employed as the radiation sources. The device may be used to determine the particle size distribution of particles in a sample by a method employing Bayesian inference.

20 Claims, 23 Drawing Sheets

(56) References Cited

U.S. PATENT DOCUMENTS

| | | |
|---|---|---|
| 5,416,580 A | 5/1995 | Trainer |
| 6,118,531 A * | 9/2000 | Hertel et al. .................. 356/336 |
| 6,122,042 A | 9/2000 | Wunderman |
| 6,373,568 B1 | 4/2002 | Miller |
| 6,507,400 B1 | 1/2003 | Pina et al. |
| 6,665,060 B1 | 12/2003 | Zahniser et al. |
| 6,765,669 B1 | 7/2004 | Pawluczyk |
| 7,151,604 B2 * | 12/2006 | Saccomanno et al. ........ 356/343 |
| 2005/0046850 A1 | 3/2005 | Chow |

FOREIGN PATENT DOCUMENTS

| | | |
|---|---|---|
| EP | 1 275 964 A1 | 1/2003 |
| WO | 9520811 A1 | 8/1995 |
| WO | 0075701 A2 | 12/2000 |
| WO | 2007066113 A1 | 6/2007 |

\* cited by examiner

Figure 16: Marginal distribution of $p_1$ from the joint distribution of 13, with the marginal mode marked with o.

Figure 19: Typical samples from the prior on the size-concentration vector (in blue) and the median in each bin (in black). Note that the vertical scale indicates not the number of droplets per unit volume in each size bin, but rather the volume of liquid in droplets as a fraction of the total air volume per decade of droplet radius.

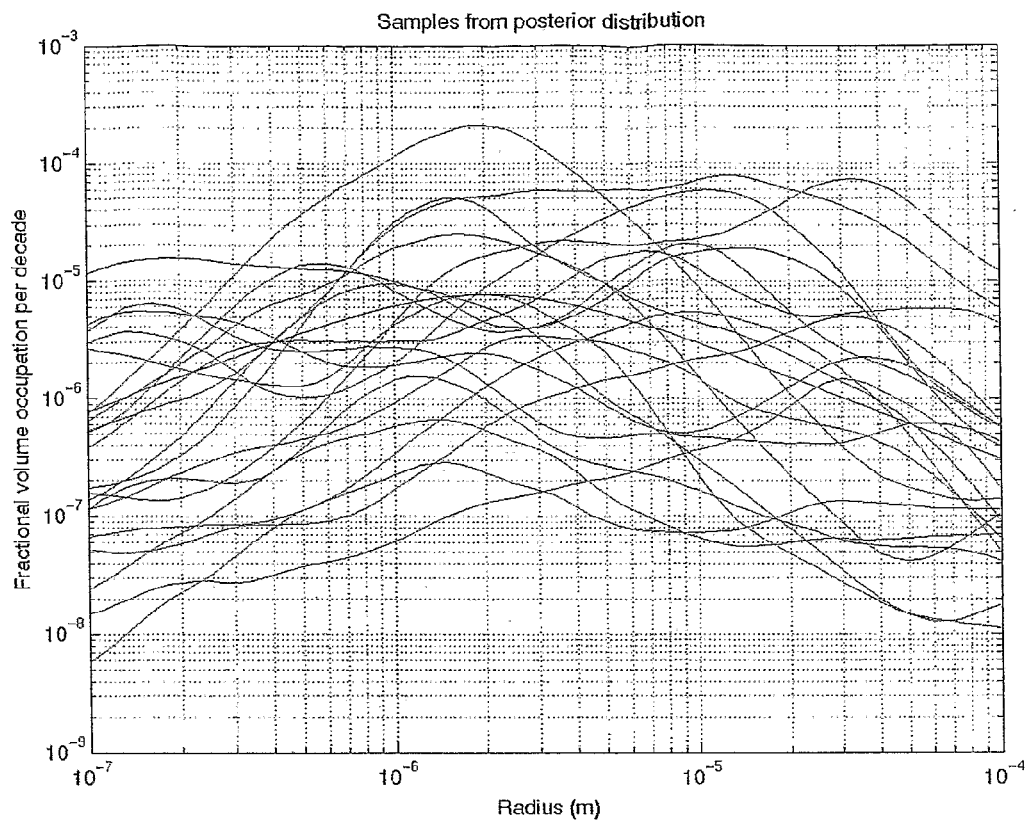
Figure 22: Typical samples from the prior distribution on size-concentration vectors x. In black is plotted the median of the prior marginal distribution for each radius. Note that the vertical axis is the fraction of the total air volume that is occupied by droplets of the given size per decade of droplet radius, on a logarithmic scale.

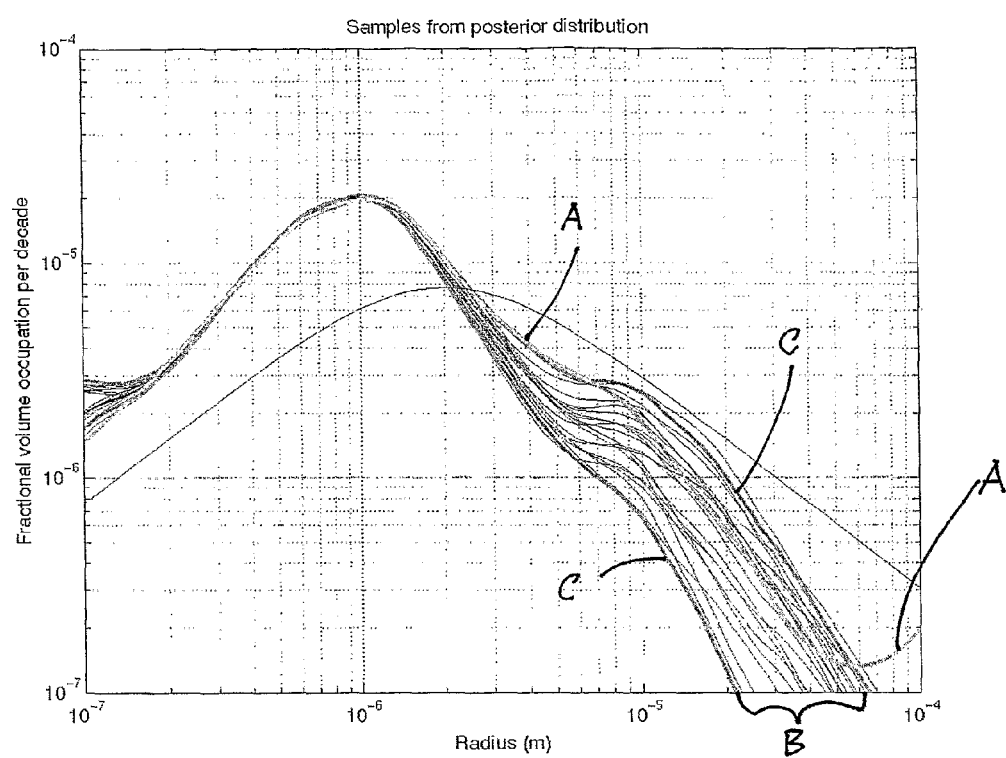
Figure 23: Typical output of the signal processing.

DEVICE AND METHOD FOR MEASURING SCATTERING OF RADIATION

This application claims priority to International Patent Application No. PCT/GB2009/000259 filed on Feb. 2, 2009, which claims priority to Great Britain Application Nos. 0801850.9 filed on Feb. 1, 2008, 0801871.5 filed on Feb. 1, 2008, and 0813679.8 filed on Jul. 25, 2008, which are hereby incorporated by reference in their entirety.

This invention relates to photometric devices, and especially to photometric devices in which a number of different beams are employed to examine a sample. As used herein, the terms "photometry" and "photometric" are employed in their broad sense to devices and methods in which radiation may be emitted from a sample at the same wavelength as absorbed by the sample or at a different wavelength. The terms thus include fluorescence, phosphorescence and chemiluminescence.

A number of arrangements have been proposed for spectral analysis of samples employing a number of beams of radiation of different wavelength. Assays that enable optical diagnostic procedures to be based on the quantitative measurement of either their spectral reflectance/absorption or fluorescence are well established. At a fundamental level this requires that the assay is illuminated by a known incident optical spectral power $P_i(\lambda_n)$ for a defined set of wavelengths $\lambda_n$ typically in the ultraviolet (UV) to near-infra red (NIR) wavelength ranges. In the basic arrangements for transmissive spectral photometric, including fluorometric, measurement the input wavelength is selected by the input filters $F_i(\lambda_n)$, $F_e(\lambda_{en})$ and pass through a beam splitter before passing to the assay (sample) and to a reference photo-detector. Systems of this type may also be configured in reflective geometry. The physical principles of the measurement are however the same as transmissive systems.

In the case of the spectral photometer, the primary measurand is the optical density of the assay $D(\lambda_n)$ where, $$D(\lambda_n) = 10 \, \text{Log}_{10}((P_t(\lambda_n)/P_i(\lambda_n))) \qquad (1)$$

and $P_t(\lambda_n)$ = the transmitted optical power

In the case of fluorescence, the fluorescent optical power $P_f(\lambda_{fn})$ excited in response to the excitation power $P_e(\lambda_{ne})$ constitutes the primary measurand. In general this requires that the excitation power be rejected by a fluorescence emission filter $F_f(\lambda_{fn})$ with a pass band centred at the fluorescence wavelength $\lambda_f$.

It can be seen that the fluorescence is emitted isotropically which also enables the fluorescence to be detected in a cone outside of the transmitted excitation beam. This arrangement is often used to minimise excitation/fluorescence cross talk. Consistency of measurement within such systems is generally maintained by a combination of:

(a) Feedback compensation of fluctuations in optical power using internal power referencing.
(b) The measurement of the interactions of the light with the same volume of assay/under the same geometrical conditions for each wavelength.
(c) The use of an assay containment vessel (cuvette) with the same geometry and dimensions for each measurement.

The extension of the system to fluorescence measurement requires the use of fluorescence filters at each measurement station. The extension of the time multiplexed systems to fluorescence measurement require that the excitation wavelengths be removed from fluorescence wavelengths by spectral filtering at the out put of system. For this purpose the inverse of the beam combining optical system in which the emitters are replaced by detectors may be used. The wavelength division multiplexed system requires the addition of a wavelength selection device (e.g. a switched filter or a monochromator) in front of the detector to select sequentially the fluorescence wavelengths. In some systems such a device is also used in front of the broad band source to select the excitation wavelengths whilst a similar device in front of the detector selects simultaneously the fluorescence wavelength in synchronisation with the latter.

This invention is concerned primarily with new means by which the light may be delivered and detected at multiple wavelengths in order to perform the measurements in accordance with the requirements (a) to (c) noted above. Current known methods for multispectral delivery and detection are summarised below.

Various multiplexing schemes may be used to enable the transition from multi-station measurement system to single station systems to be made. In the case of multistation systems, light from a spectrally broad band source is divided (typically by either multiple beam splitters or bifurcated optical fibre, BOF) between the n measurement stations each with different spectral filters $F_1$ to $F_n$. The single station systems use either Time Division Multiplexing (TDM:) or Wavelength Division Multiplexing WDM:).

In the TDM system the assay is sequentially illuminated and detected at defined times $t_n$, by each at different wavelengths $\lambda_1 \ldots \lambda_n$. For the WDM systems the assay is illuminated simultaneously by the wavelengths $\lambda_1$ to $\lambda_n$ (i.e. by spectrally broad band source) and the individual wavelengths $\lambda_n$ selected at the output using a wavelength dispersive device WD such as a spectrometer or monochromator. Types of modulation device that are often used in conjunction the different types of input light sources for the above systems are summarised in Table 1.

TABLE 1

| | Light source | Wavelength/ polarisation selection | Detection |
|---|---|---|---|
| A | Broad band | Mechanically switched spectral and polarising filters | Multiple fixed detection array with static spectral and polarising filters |
| B | Broad band | As above | Single moving, detectors with mechanically switched spectral and polarising filter. |
| C | Broad band | Mechanically switched spectral and polarising filter | Single moving spectrometer with mechanically switched spectral and polarising filters |
| D | Broad band | As above | Multiple fixed spectrometer array, with static spectral and polarising filters |
| E | Dichroic combination of discrete LED/Laser diode source (FIG. 3) | Electronic time multiplexed switched | Multiple fixed detector array with static spectral and polarising filters |

The discrete light sources are typically combined using fibre combiners, dichroic combiners in which light from a number of sources are reflected by a number of dichroic mirrors into a single beam, Additional methods include a focusing grating combiner and a fused dichroic optical fibre combiner.

Systems A to D are based on spectrally broad band sources and all have the common limitation that they require either a single or multiple combination of moving parts (such as filter switches, detector translation mechanisms etc) to achieve the required level of multiple channel and multiple wavelength operation. This introduces two major disadvantages:
(a) reduced reliability due to the presence of moving parts, and
(b) extended measurement periods due to the time required to switch mechanically between channels.

The measurement periods that can be achieved in practice within the limitations imposed by (b) are longer than those required typically for real time measurement of dynamically varying systems such as droplet and particle size distributions.

System E in which multiple discrete sources such as LEDs are combined using a chain of dichroic beam combiners may be electronically switched between channels and thereby operate in a high speed, time multiplexed mode. However, the extension of this beam combination geometry to a relatively large number of wavelengths that is desired according to the present invention makes it optically complex and expensive. In addition the polarisation state of the sources is likely to be modified as the result of reflection from the individual dichroics.

According to one aspect, the present invention provides a photometric device which comprises an array of radiation sources that are spaced apart from one another, and which are operable to generate radiation that differs from that generated by at least one other radiation source in the array, a lens arrangement for directing radiation from the radiation sources to a region of space, and at least one radiation detector for receiving radiation from the region of space.

The device according to the invention has the advantage that it enables multi-spectral photometric detection (including fluorometric and time resolved fluorometric detection) to be performed, but is relatively simple and can be made as a robust unit, for example a hand-held unit, with no moving parts. The device eliminates the use of multiple dichroics, beam splitters and bulky bifurcated optical fibres in beam combining configurations, and can be made at a relatively low cost as a result of compatibility with low cost components and manufacture.

According to this aspect of the invention, the region of space may, in operation, include a sample to be investigated. The sample may be held in a sample holder, for example a cuvette or other arrangement that is appropriate to the particular application. For example, a number of cuvettes located on a conveyor may pass through the region of space, or a fluid sample may be passed along a conduit e.g. a macro or microfluidic channel, or droplets may be constrained in an air flow. Where the sample is a mist of droplets, it may simply be located in the region of space with no constraint. The device may be provided with a number of radiation detectors, preferably the same number of detectors as the number of radiation sources. According to this embodiment the device may include only a single radiation detector or an array of detectors. The radiation detectors may be spaced apart from one another and arranged so that radiation emerging from the region of space in a single line may pass through a number of dichroic mirrors to separate radiation of different wavelengths. Preferably, however, the radiation detectors are spaced apart in a direction transverse to the direction of the radiation emerging from the region of space so that radiation may be transmitted from at least one radiation source to a radiation detector through the region of space and that radiation can be received by the other radiation detectors after having been scattered by a sample located in the region of space (whether the sample is held in a sample holder or not).

In such a case it is possible to design the device such that some of the radiation detectors will be in alignment with a radiation source and the sample holder so that it will receive transmitted radiation, while other radiation detectors will not be in alignment and so will be able to detect radiation scattered by the sample. Thus the device preferably includes a generally circular array of radiation detectors that are located about the axis of the array of radiation sources, each radiation detector being operative to receive radiation emitted by one of the radiation sources that has passed through the region of space.

If the device has n radiation sources arranged symmetrically in a ring about the axis of the device, and n radiation detectors, then radiation emanating from one of the radiation sources maybe detected at each of the n detectors, one of the detectors receiving radiation that has been transmitted by the sample, and the other n−1 detectors receiving radiation that has been scattered by the sample. Thus, the n radiation sources will correspond to $n^2$ channels through the sample. The number of radiation sources and detectors will normally depend on the intended purpose of the device. For example, if the device is used for process control or monitoring, it will typically contain from two to four sources and detectors, while if the device is used for high throughput clinical testing, the device may include from four to eight sources and detectors. In one preferred aspect discussed more fully below, where the device is used in industrial processes or in the pharmaceutical industry for determining particle/droplet size distributions, it may include typically eight sources and detectors, giving 64 channels through the sample.

According to another aspect of the invention, a waveguide for example an optical fibre, may be located between the region of space and the detector or detectors so that radiation may be transmitted from the region of space to the radiation detector(s) via the waveguide. In this case, the sample is preferably located between the waveguide and the detector(s), and the waveguide may act as a homogeniser for mixing the modes of the radiation from the radiation sources to the sample, for example in order to remove or reduce speckle generated in the case where laser diodes are used as the radiation sources.

The device according to the invention may be employed in a number of ways. For example it may be used for monitoring of particles or droplets or process control, or it may be employed for multi-wavelength spectral photometry (including fluorescence) imaging. In addition, and as discussed more fully below, it may be employed for quantitative droplet/particle size measurement. Whichever mode the device is employed in, but especially for multiwavelength imaging and droplet/particle size measurement, the device may include a time division multiplexer for time division multiplexing the radiation sources so that, in operation, a sample will be illuminated by radiation from only one of the radiation sources at any time.

Several devices in accordance with various aspects of the invention will now be described by way of example with reference to the accompanying drawings in which:

FIG. 22 shows typical samples from the prior distribution on size-concentration vectors x in the droplet size determination; and FIG. 23 is a typical output of the signal processing in the size-concentration determination.

The device according to the first aspect of the present invention is intended to perform single station multi spectral photometric (including fluorometric) measurements preferably in accordance with a time multiplexed system configuration.

Figure 1:
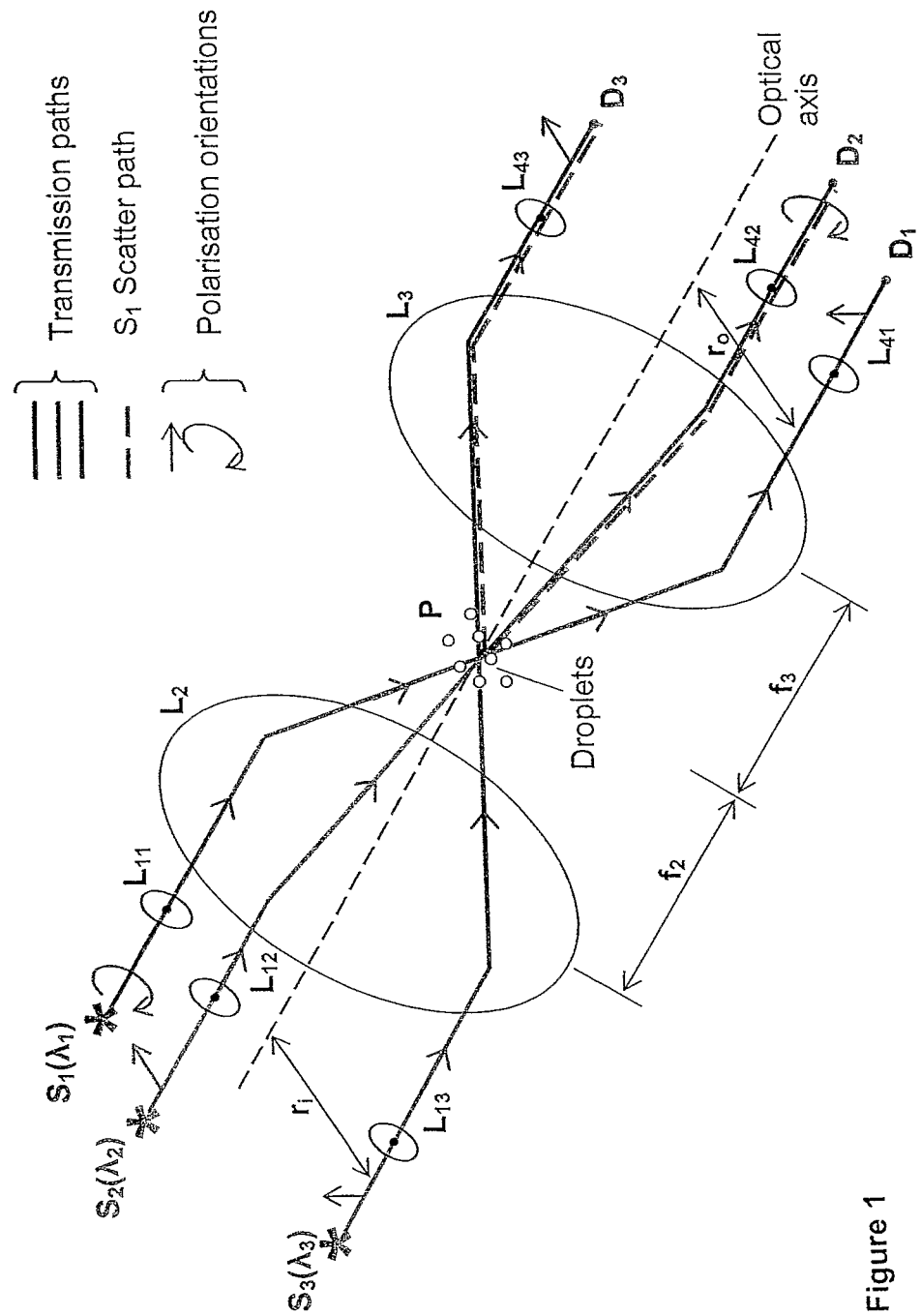
FIG. 1 is a schematic representation showing the principle of one form of device according to the invention.

The basic optical geometry of the co-axial sensor is shown in FIG. 1 for the case of three collimated illumination sources $S_1, S_2, S_3$ with wavelengths $\lambda_1, \lambda_2, \lambda_3$ and polarisation states of right circular, horizontal and vertical respectively. The sources are located in the circumference of a circle of radius $r_i$ in a plane parallel to that of the focusing objective $L_2$ of focal length $f_2$. Each source is collimated by the lenses $L_{1n}$. (n=1, 2, 3) The polarisation orientation of the illumination may be selected by a polarising filter placed in the collimated beam. The circular array of collimated beams are incident normally on $L_2$ and bought to focus in a region centred about a point P in the common optical axes and focal planes of $L_2$ in which a sample to be investigated may be located (in this case a cloud of droplets) and the collection objective $L_3$ (focal length $f_3$). In operation the droplet cloud passes through the region surrounding P and the transmitted and scattered light fields are collected and, by symmetry, collimated by $L_3$. The lenses $L_{4n}$ (n=1, 2, 3) focus these collimated light fields in the plane of the detectors $D_1$, $D_2$, and $D_3$, respectively. The polarisation orientation of the detected beam may be selected by a polarising filter placed in the collected collimated beam. It will be seen from FIG. 1 for the geometry shown that the $S_1$ right circularly polarised beam is detected in vertical polarisation in transmission by $D_1$ and in circularly and horizontally polarised scatter by $D_2$ and $D_3$ respectively. Similarly, $S_2$ is detected in transmission by $D_2$ and in scatter by $D_{i1}$ and $D_3$, and $S_3$ in transmission by $D_3$ and scatter by $D_1$ and $D_2$. It follows from this that an n-channel input and detection sensor of this geometry result in $n^2$ detection channels consisting of n transmission and $n(n-1)$ scatter channels each corresponding to different combinations of polarisation, wavelength and angle.

Figure 2:
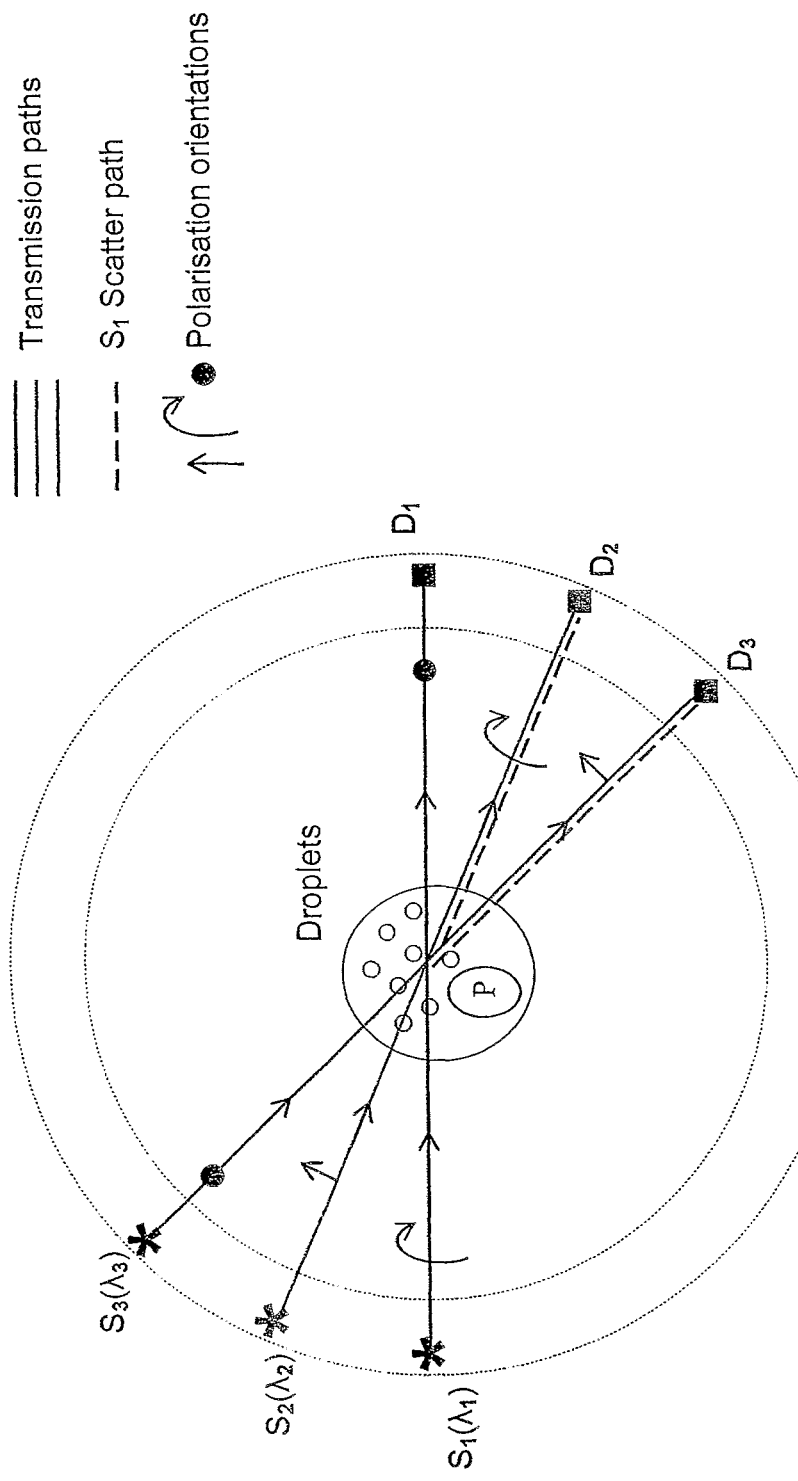
FIG. 2 is an alternative configuration of the sensor based on coplanar optics in a cylindrical geometry.

An alternative configuration of sensor based on a cylindrical geometry and co-planar optics is shown in FIG. 2. In this arrangement the individual illumination and detection modules are mounted co-axially in the surrounding cylindrical optical housing. The common focal points of the latter are centred at P which are located at the centre of a cylindrical mounting. This is a relatively simple system to manufacture but has the disadvantage, relative to the above coaxial geometry, that the larger angles of illumination and detection in combination with the cylindrical housing limit droplet access and make the sensor less flexible in use.

In practice all of the $n^2$ measurements must be performed within a period during which the particle size distribution within the measurement zone is stationary. For this purpose it is preferred to use a time multiplexed mode of operation so that within the 'stationary period' the particles are successively illuminated and detected for each of the available angle, wavelength and polarisation state. For practical applications the duration of the 'stationary period' is typically 10 msec to 1.0 msec. Thus it is preferable to use illumination sources such as Light Emitting Diodes (LEDs) or Laser Diodes, which can be switched on and off at high frequencies. It is important to note that, if Laser Diodes are used, they will generate speckle noise in the scattered field due to their coherence. This should not be a problem provided that this speckle structure is spatially integrated over a sufficiently large receiving aperture. LEDs have intrinsically low coherence and will not generate speckle noise of any significant contrast. The device has been shown above having three radiation sources and detectors for the sake of clarity, however more sources may be employed as desired depending on the application. In practice a combination of eight sources and detectors is used to give a 64 channel sensor.

Figure 3:
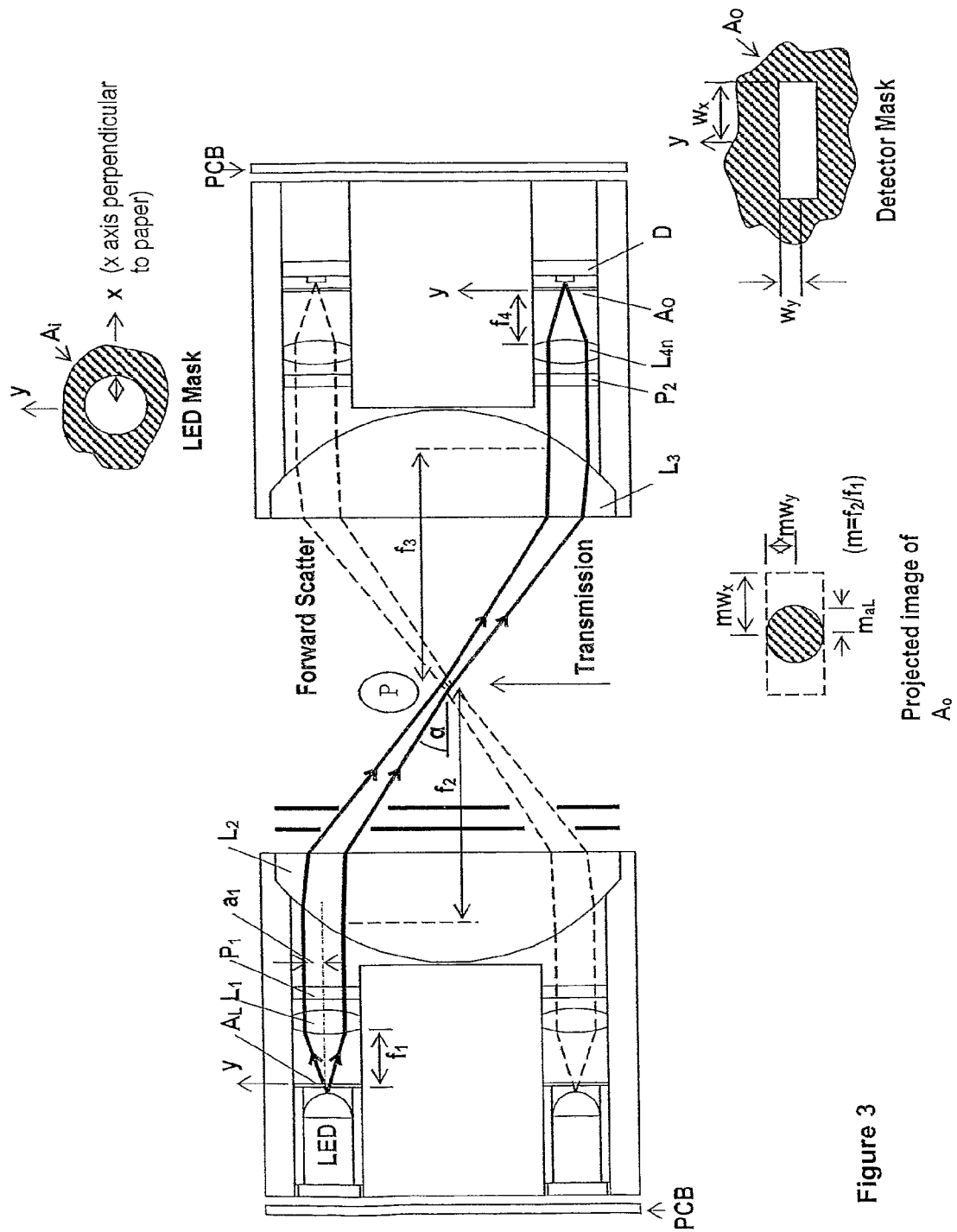
FIG. 3 is a side elevation of one embodiment of the device according to the invention.
Figure 4:
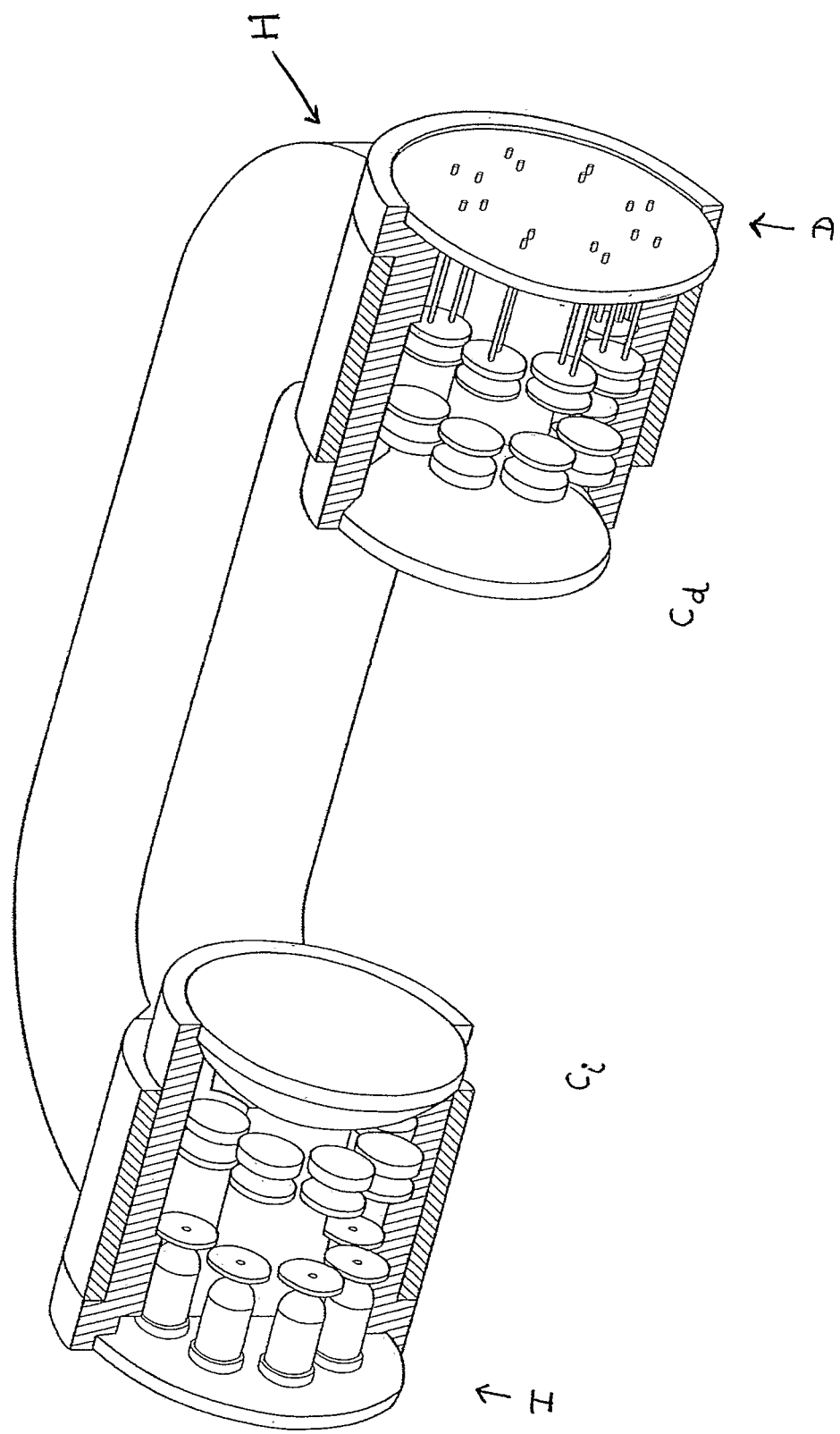
FIG. 4 is a perspective view of the device shown in FIG. 8.

FIG. 3 is a side elevation of one form of device according to the invention for particle size determination, and FIG. 4 is a perspective view thereof. The device has a generally cylindrical shape, and has eight LEDs that are each located uniformly about the axis of the device behind a mask $A_L$. In this module the LED light source is limited spatially by a circular aperture in the LED mask $A_L$ placed in direct proximity to the front face of the LED. The divergent source of area $\pi a_i^2$ ($a_i$=radius of LED mask aperture) is collimated by the lenses $L_{1n}$ and is incident normally on the common focusing objective $L_2$. A polarising filter $P_{1n}$ is placed in the collimated beam in order to create the required orientation of polarisation. $L_2$ and $L_3$, consist typically of planovex or aspheric singlet lenses with focal lengths $f_1$ and $f_3$ respectively. The input illumination modules are mounted around the circumference of a circle of radius $r_i$ (FIG. 1) and the corresponding radius $r_o$ for the circular array of complimentary detection modules is equal to $r_i f_3/f_4$. In a preferred system $f_2$ and $f_3$ are equal and $r_o = r_i$. When $f_2 = f_3$, the detection module has, by symmetry, the same geometry as that of the illumination module. The collected light fields are collimated by $L_3$ and are imaged in the plane of the detector mask by the lenses $L_{4n}$ after passing through the detection polarising filter $P_{2n}$. The detector has an active area greater than that of the mask aperture and is placed directly behind the aperture. The mask may be either circular or rectangular (as shown). The latter geometry makes the system less sensitive to misalignment. In practice it has been found that the intrinsic self aligning nature of the system (see below) is sufficient to enable the use of a circular aperture. The dimensions of typical components are summarised shown in Table 2 below:

TABLE 2

| | |
|---|---|
| $f_1, f_4$ | 7.7 mm |
| $f_2, f_3$ | 35.0 mm |
| m | 4.5 mm |
| $a_L$ | 0.22 mm |
| $a_1$ | 1.9 mm |
| $m\, a_L$ | 1.0 mm |
| $\alpha$ | 0.28 radians |

A representative opto-mechanical assembly of the co-axial device sensor is shown in FIG. 4. Here the illumination and detection modules are mounted in the circular array of cylindrical location bores machined in the cylindrical carriers I and D respectively. The illumination and detection optical axes are set parallel to those of the illumination and detection objectives $L_2$, $L_3$ by co-axially locating the carriers I and D with respect to the objective carriers $C_i$ and $C_d$ respectively. The assembled illumination and detection units I,$C_i$ and D,$C_d$ are axially aligned and focused by mounting them in a common coaxial carrier H. Under these conditions either the illumination or detection unit may be rotated about the optical axis to establish circumferential alignment. This adjustment may be eliminated by keying the two units with respect to a common radial location.

An important feature of the above design is that the LED and detector apertures operate as small field stops and prevent cross talk between adjacent channels. For example, in the absence of particles, the power of the light in the scatter channels is measured to be typically $10^{-5}$ that in the transmitted channels. The cross talk is not observed to increase significantly when, as is often required in practice, a transparent cylindrical particle containment vessel is placed perpendicular to the optical axis with its central axis intersecting P.

The sensor shown in FIG. 3 may be constructed by mounting individual laser collimation and detection modules of the type described above in the cylindrical housing as shown.

In a particularly preferred embodiment of the optical sensor, as shown in FIG. 1, the locations of the transmitters, receivers, and polarisations for each channel are as described in this subsection as follows.

To establish a coordinate system the "North pole" can be considered to be at the centre of the circle of receive lenses and the "South pole" to be at the centre of the circle of transmit lenses. The "Greenwich meridian" can be defined as as an arbitrary great circle joining the two poles on the surface of the sphere. With respect to these defined objects "latitude" and "longitude" will have their conventional meanings.

All transmitters are centred at latitude $-(\pi/2-0.28)$ radians and all receivers at latitude $+(\pi/2-0.28)$ radians. The transmitters are numbered 1 to 8, with transmitter 1 at 0 longitude, and each successive transmitter having an additional $\pi/4$ radians West longitude. The receivers are numbered 1 to 8, with receiver 1 at 0 longitude and each successive transmitter having an additional $\pi/4$ radians West longitude. The centre wavelengths of the transmitters are from 1 to 8 in order 365, 467, 505, 593, 631, 740, 780, 940 nm respectively. The transmitters from 1 to 8 carry polarisers of type 0; 1; 3; 5; 2; 4; 3; 1 respectively (where the types are defined below). The receivers from 1 to 8 carry polarisers of type 1; 2; 4; 3; 2; 5; 6; 2 respectively (where the types are defined below).

Polariser types are defined as follows:
  0. No polariser.
  1. Polarised parallel to the plane containing the centre of the polariser and the North and South poles.
  2. Polarised at right angles to polariser type 1.
  3. Polarised $\pi/4$ anticlockwise from meaning 1, looking along the light beam towards its destination.
  4. Polarised $\pi/4$ clockwise from meaning 1, looking along the light beam towards its destination.
  5. Polarised right circularly.
  6. Polarised left circularly.

Here, a right circular polariser means one that permits passage of right circularly polarised light, which in turn means light for which at a fixed point in space the electric field vector rotates anticlockwise as seen by an observer looking from the origin of the light towards the destination of the light.

Figure 6:
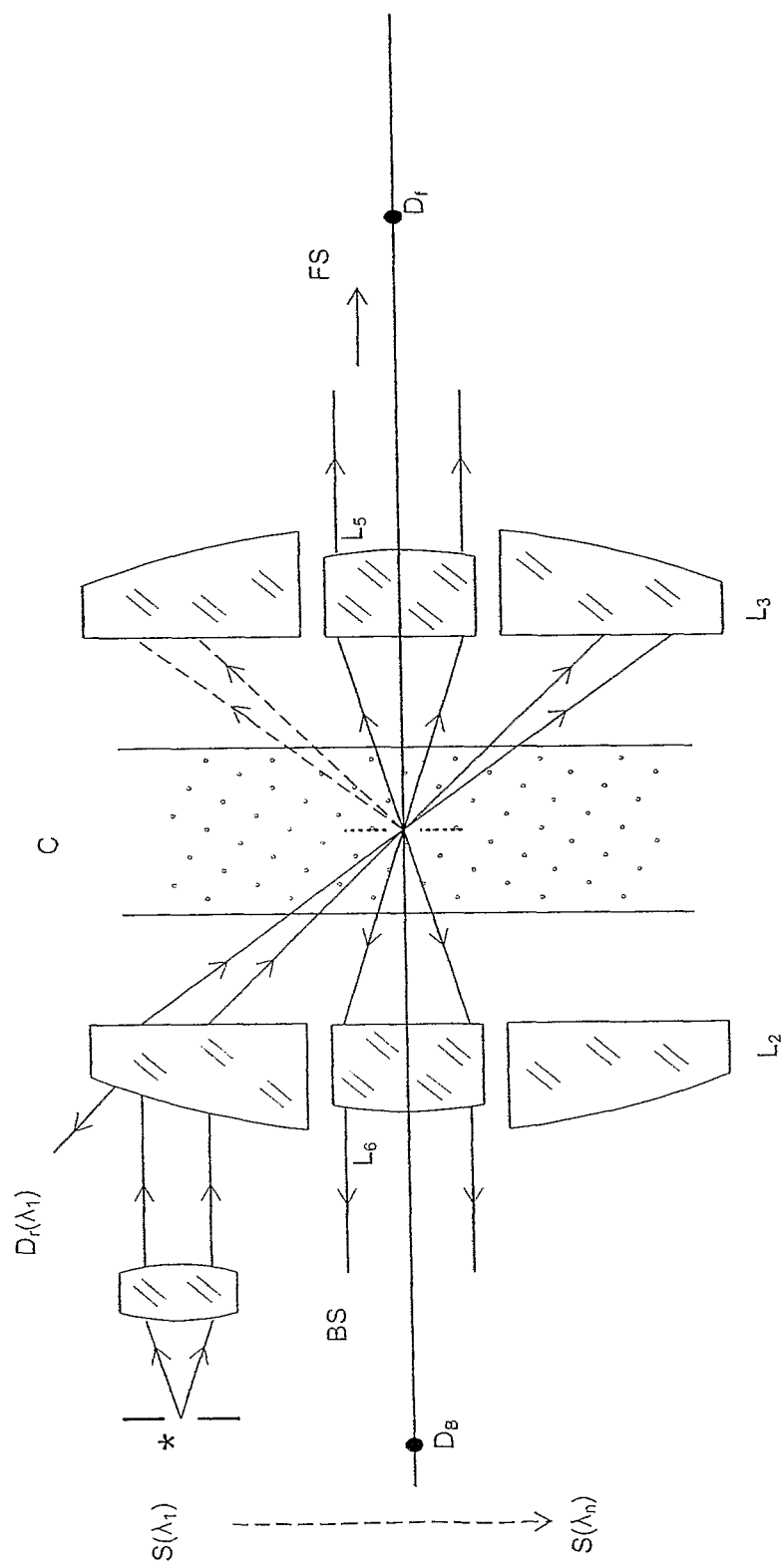

The above defines the polarisation orientation for a given polariser lying in the surface of sphere that has its centre at the common focal point of the illumination beams P, and the North-South axis coincident with that of the central optical axis as shown in FIG. 6. In practice the polarisers are mounted parallel to the plane of the detector objectives $L_{41}$, $L_{42}$, $L_{43}$ . . . and the polarisation orientation in this plane will correspond to that unfolded from this spherical plane.

The device as shown in FIGS. 3 and 4 thus enables a sample to be analysed by a number of beams of radiation of different wavelength and/or polarisation (horizontal, vertical or circularly). The device may for example be employed for parametric measurement or for multi-spectral fluorescence photometry. The device may be used to analyse samples in free space, that is to say, where the sample is supported at the point where the beams of radiation from the radiation sources converge, or it may be employed for other purposes, for example for imaging, e.g. fluorescence imaging.

The radiation sources arranged about the axis of the device may be time division multiplexed so that in each time slot radiation emitted by one of the radiation sources may be detected by each of the radiation detectors.

Figure 5:
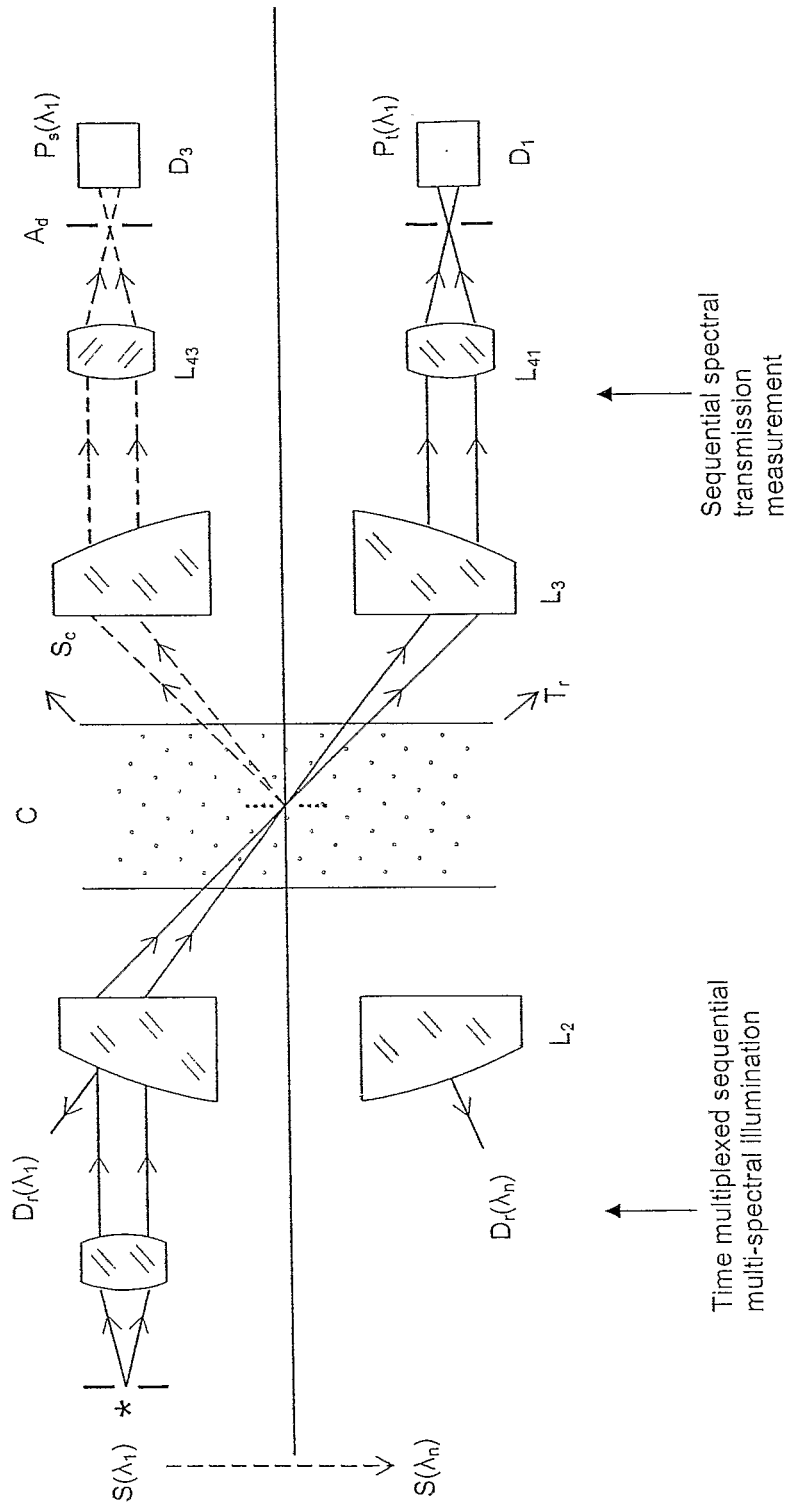
FIGS. 5 to 8 are sections through the device in various modes of operation.

FIG. 5 is a section through a modification of the device shown in FIGS. 3 and 4. This figure shows how the ring illumination geometry enables spatial separation of the time multiplexed transmitted (Tr) and scattered beams (Sc) at the different wavelengths.

The device shown in FIG. 5 includes the following features that enable the general requirements (a) to (c) mentioned above to be satisfied:
  (a) The internal reference $D_1(\lambda_n)$ is derived from the back reflection from the lens $L_2$ or other suitable surfaces.
  (b) The detector aperture $A_d$ constitutes a confocal stop that limits the detection zone to a volume centred at focus that is appreciably the same for all wavelengths given the same geometry of cuvette.
  (c) Polarising filters may be introduced in the input and output beam paths for the purpose of polarisation dependant measurements.
  (d) A hole, preferably blackened, and ideally concentric to the optical axis is present in the common source and detector objectives $L_2$ and $L_3$ to minimize inter-channel scatter and cross talk.

FIG. 6 shows an alternative configuration in which the forward and back-scatter for all wavelengths is collected respectively by $L_5$ and $L_6$ mounted in the holes in the source and detector objectives for minimising inter-channel scatter and cross-talk central to $L_2$ and $L_3$ and detected by $D_s$ and $D_b$.

Figure 7:
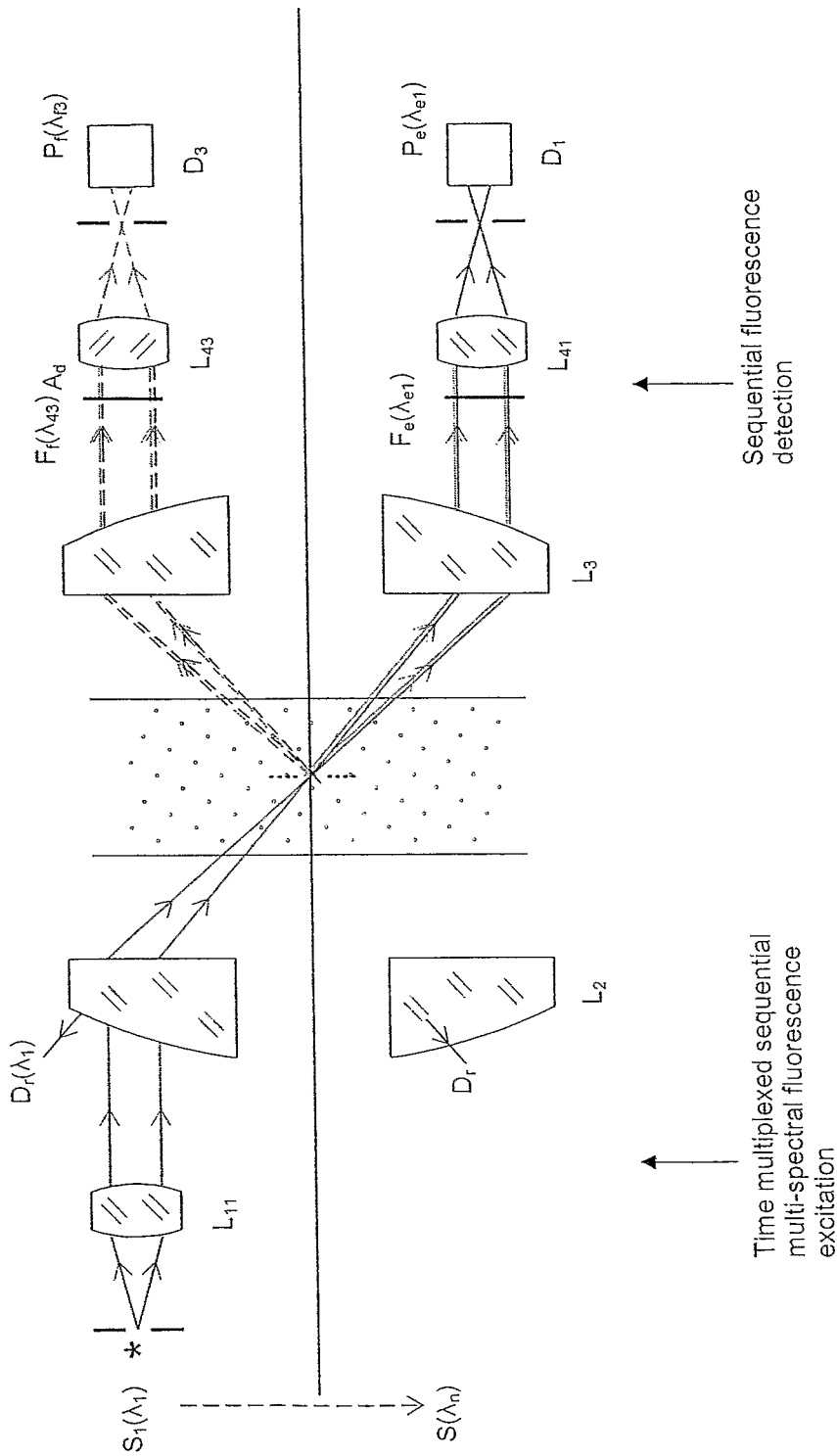

FIG. 7 shows how the ring illuminator geometry may enable the spatial separation of time multiplexed fluorescent excitation beams and transmitted excitation and fluorescence beams. In the detection section at $D_1$ the transmitted excitation beam P is filtered by $F_e(\lambda_{en})$ to eliminate the fluorescence light. A component of the isotropically emitted fluorescence light is collected and detected at $D_3$ after passing thought the fluorescent filter $F_f(\lambda_{f3})$ for the fluorescent wavelengths $\lambda_{f3}$ excited $\lambda_{ef}$. As an example, FIG. 9 shows the filter geometry for 8 channels operated in this way that enables four fluorescent wavelength and corresponding excitation powers to be measured sequentially.

Figure 8:
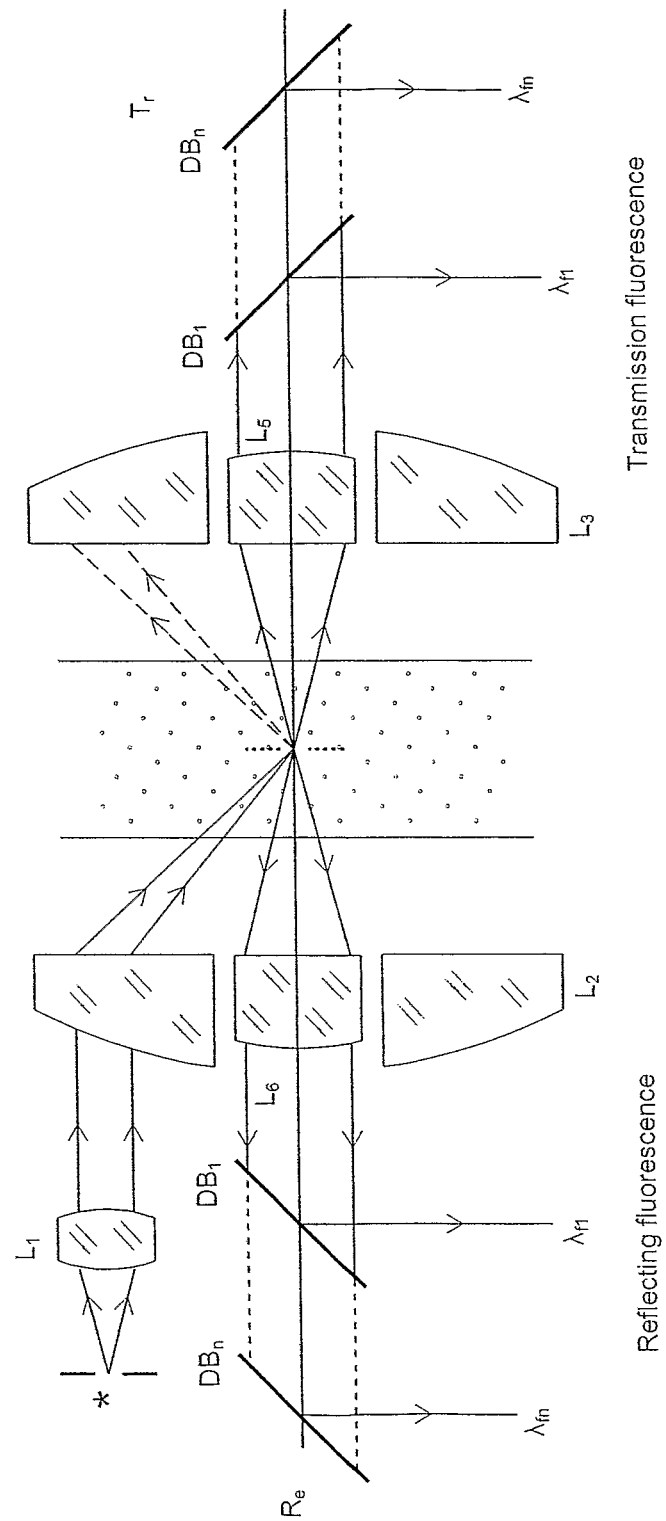

FIG. 8 shows the fluorometric equivalent of the photometric system shown in FIG. 6 in which the combination of dichroic beam splitters and fluorescent filters $DB_n$, $F_f(\lambda_{fn})$ are used to measure the individual fluorescence wavelengths.

Figure 9:
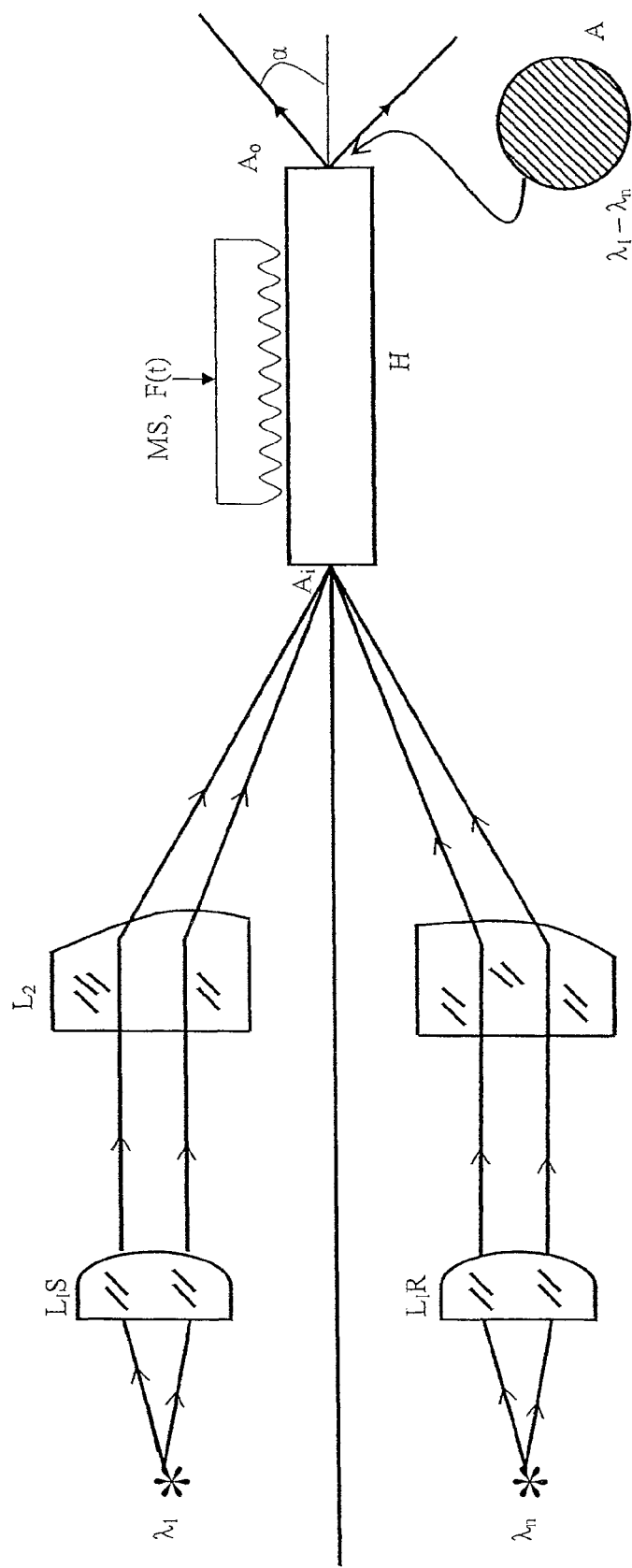
FIGS. 9 to 11 are schematic sections through devices that employ an optical waveguide as a homogeniser.

FIG. 9 shows an alternative form of device according to the invention. This form of device comprises an array of light sources generating light of wavelength $\lambda_1$ to $\lambda_n$. The device includes lenses $L_{11}$ and $L_{1n}$ for collimating the light from the light sources, and a common objective $L_2$ for focusing the light beams at the input aperture $A_i$ of an optical waveguide H that acts as an homogenising element for the light and is located in the common focal plane of the device. The waveguide may be a rigid waveguide or a multimode optical fibre. In this configuration the maximum angle of incident illumination is within the Numerical Aperture NA of the waveguide. The homogenisation of the individual beams of different wavelength incident on the input aperture $A_i$ of the waveguide results from their multi-modal propagation within its waveguide structure. For appropriate dimensions of wave guide, the output aperture $A_o$ of H is thereby illuminated uniformly by all wavelengths. The latter couple into an output beam of light that diverges about the central axis of H with a half angle α defined by its numerical aperture (NA).

Figure 10:
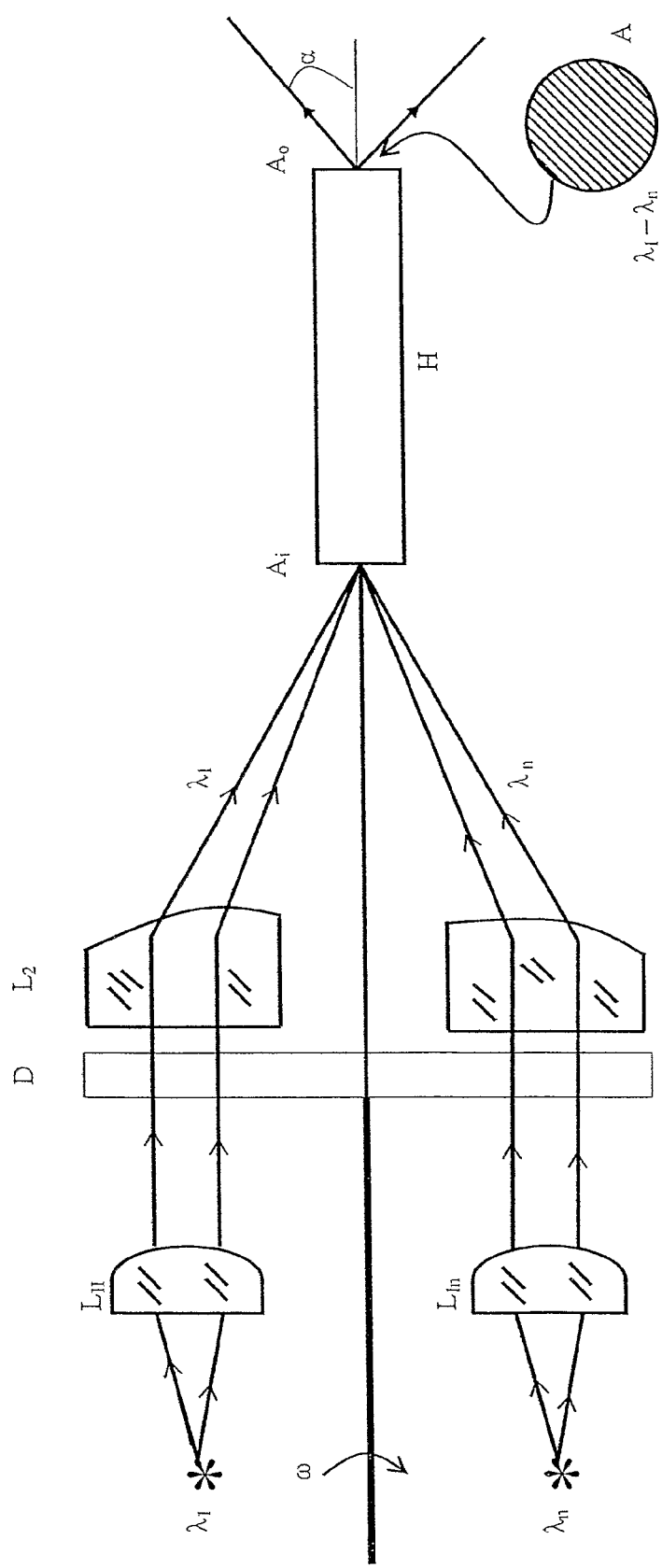

The radiation sources employed in the device according to the invention may be chosen from any of a number of sources, and are preferably fowled as light emitting diodes (LEDs) or laser diodes. In a number of applications (e.g. fluorescent molecular imaging) the light sources $\lambda_1$ to $\lambda_n$ will consist of spectrally narrow band laser diodes which results in the superposition of coherent speckle noise upon the output beam due to the randomly phased interference that occurs between the mutually coherent propagating modes in H. This degrades image resolution and has to be eliminated for imaging application. In view of this, the device may include a dynamic mode scrambler MS which may subject the waveguide to a time varying sinusoidal perturbation, thereby to temporally average the speckle and flatten spatially the multispectral light field at the output of the homogeniser H. Alternatively, as shown in FIG. 10, a rotating diffuser D may be used to average the speckle and flatten the light field. A holographic diffuser is preferred in the case of the rotating diffuser configuration because this device has controlled beam divergence and minimizes light loss.

The phase volume of an optical emitter, $\theta_e$ is given by $$\theta e = A_s \Omega_s$$

where, $A_s$=the light emitting area $\Omega_s$=the solid angle into which the optical power P(W) is emitted ($\Omega_s$=4 $\sin^2$ α/$_2$, where α=half cone angle of divergence of source)

If the solid angle of acceptance of the homogenising element H of area $A_H$ is $\Omega_H$ and divided between n sources of the same beam phase volume, the solid angle of the homogeniser available into which each source may be coupled into is therefore $\Omega_H$/n. All of the optical power from the emitter may (neglecting reflection losses etc.) be coupled into the homogeniser provided that $$A_S \Omega_S \leq A_H \frac{\Omega_H}{n}$$

When $A_s \Omega_s \geq A_H \Omega_H / n$, the coupling efficiency, ε, is given by, $$\varepsilon = \frac{A_H \Omega_H}{n A_S \Omega_S}$$

These forms of beam combiner have the advantage that they are intrinsically self-aligning and eliminate the need for multiple dichroics, bulky bifurcated optical fibres, beam splitters and filters. They may be used as an input element for any time multiplexed or broad band (i.e. as a synthesized broad band source) photometric/fluorometric application.

Figure 11:
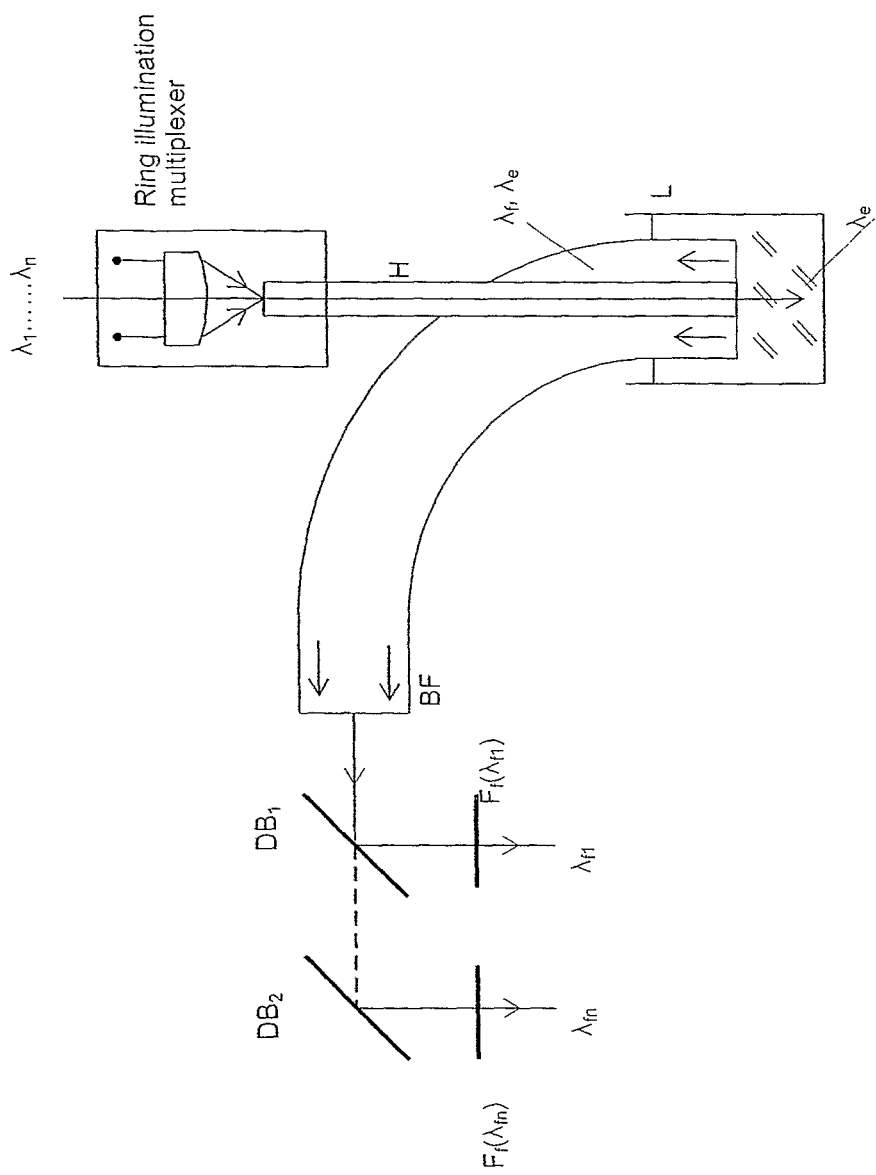
Figure 12:
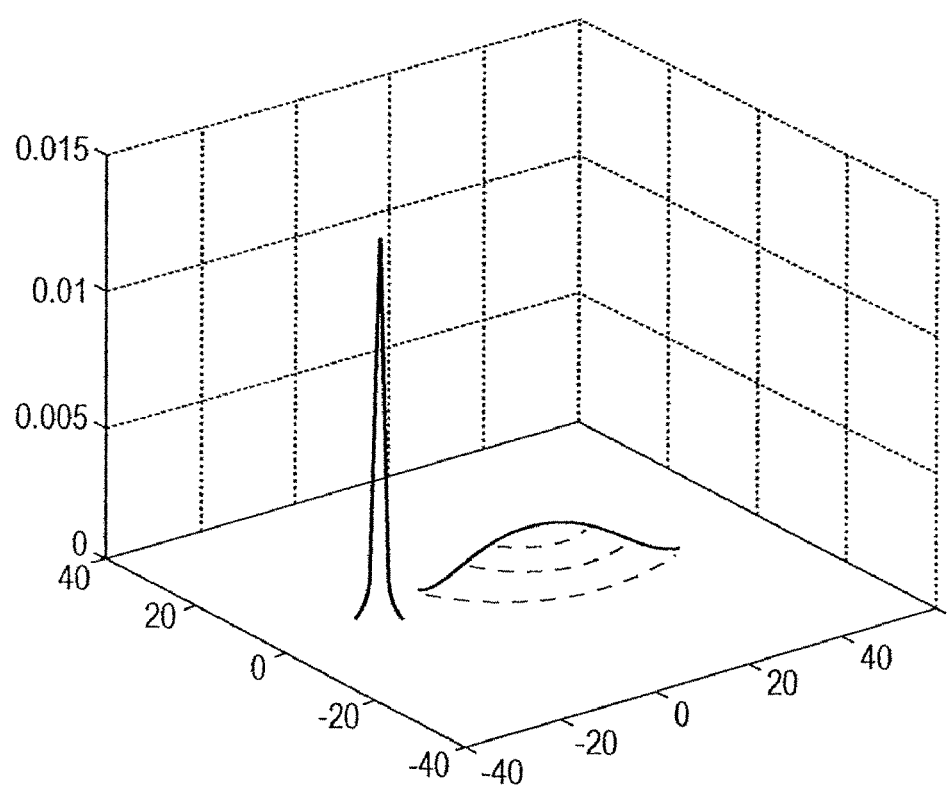
FIGS. 12 to 18 are graphical representations of various distributions referred to in the explanation of Bayesian inferential analysis.

It is, however possible to employ a bifurcated optical fibre for detection of output light in fluorometric measurement. A specific configuration of this is shown in FIG. 11. In this arrangement, a ring illumination multiplexer according to the invention and as shown in FIG. 11 or FIG. 12 generates radiation of wavelength $\lambda_1$ to $\lambda_n$ which is injected into the input aperture of an homogeniser H in the form of an optical fibre. The output of the optical fibre H injects light into the sample to be tested, and the energising light $\lambda_e$ together with the fluorescence light $\lambda_f$ is injected into the bifurcated pickup fibre BF. The reflected fluorescence light that is emitted by the bifurcated optical fibre BF can be split into its components $\lambda_1$ to $\lambda_n$ by any appropriate means, for example by means of dichroics.

It is noted that the homogeniser will not in general be polarisation maintaining and that polarisation dependant measurement is therefore limited to a single polarisation state introduced at the output of the homogeniser.

The device according to the invention may be employed in a number of applications where fluids containing particles (either solid particles or droplets of liquid) are tested. For example the device may be used to measure droplet size concentration spectra for pharmaceutical applications, for example for inhalers that are intended to deliver asthma drugs or insulin. Since only certain droplet sizes reach the bronchioles (asthma) or alveoli (insulin for diabetes) where they exert their beneficial effect, while others may reach other parts of the body and cause undesirable side-effects, adequate control of this size-concentration spectrum is very important. In other applications, the device may be used to determine droplet size spectra for sprayed paint or for supplying water, nutrients or pesticides to crops. Alternative applications include monitoring of dust particles in a variety of industrial applications, analysing inks or other liquids for counterfeit detection or detection of flavours or other materials in foodstuffs.

The scattering data obtained by the device according to the invention may be used to obtain the particle size distribution of a sample from the scattering equations developed by Gustav Mie over 100 years ago, by a method involving Bayesian inference. Before the method is described in detail, the general background of probabilities and then of Bayesian inference is described below.

1 Detailed Account of the Relevant Parts of the Prior Art of Bayesian Inference 1.1 Probability Theory 1.1.1 Probability Density The probability of a continuous random variable taking an exact particular value is 0; for example the probability that a Gaussianly-distributed (i.e. Normally distributed) variable X of standard deviation 1 and mean 0 being exactly 0 is 0—and the same for any other particular value. Nonetheless the probability that X lies between −0.0001 and +0.0001 is not zero, but approximately 0.0002/$\sqrt{2\pi}$; the number 1/$\sqrt{2\pi}$, by which the length of the interval was multiplied, is the probability density of X at 0. Thus the probability density is not the same as the probability. This is easily confused as both the probability of X taking a particular value and the probability density of X at that value will both be denoted P(X) throughout in line with normal custom and practice.

1.1.2 Conditional Probability

Suppose that A, B are events (i.e. A,B∈M, the set of events, or objects whose probability can be measured) such that P(B)≠0. Then the conditional probability of A given B, written P(A|B), is defined to be $$\frac{P(A \cap B)}{P(B)},$$

where P(A∩B) means the probability that both A and B occur. Herein we will adopt the usual convention of writing P(A,B) as shorthand for P(A∩B).

As practical examples
- If B is the event that an ordinary die is thrown and the value is divisible by 3, and A is the event that the same value is divisible by 2, then P(A|B) is 0.5.
- if B is the event that two dice are thrown and the sum of the two values is divisible by 3, and A is the event that the same sum is greater than 7, then P(A|B) is 5/12.

1.1.3 Chain Rule

Suppose we have two events A and B, and we want to know the probability that both occur, i.e. we want to know P(A,B). Then it is all too easy to assume that we can write P(A,B)=P(A)P(B); this is however in general false. To see this note that if two dice and consider X the sum of the two values, and set A to be the event that X is divisible by 2 and B to be the event that X is greater than 7, then $$P(A) = \frac{1}{2}, P(B) = \frac{5}{12},$$

but $$\frac{P(A \cap B)}{P(B)},$$

To emphasise how important it is that the above formula is false, let us note that if it were true then Bayesian inference would have no value whatever—indeed it would be impossible to deduce any fact from any other fact. The correct formula, as can be seen from the definition of conditional probability and an additional argument to cover the possibilities that P(B)=0 or that P(A)=0, is $$P(A,B)=P(A)P(B|A)$$

or equally $$P(A,B)=P(B)P(A|B).$$

These formulae are the simplest form of the chain rule. Of course, if P(A|B)=P(A), then the second formula will reduce to the formula that is in general false. If P(A|B)=P(A), then we say that the events A and B are independent, written A⊥B. Similarly we define events A and B to be independent given an event C if P(A|C)=P(A|B,C), and if so we write A⊥B|C.

For two random variables X and Y to be independent, so that we can say P(X,Y)=P(X)P(Y), it is necessary that we have independence of every pair of events A and B such that A belongs to the smallest σ-field $\sigma_X$ with respect to which X is measurable and B belongs to the smallest σ-field $\sigma_Y$ with respect to which Y is measurable. This is a very strong condition. Likewise to have X and Y be independent given a third random variable Z, we require A⊥B|C for any A∈$\sigma_X$, B∈$\sigma_Y$, C∈$\sigma_Z$. In order to be able to write P(X,Y,Z)=P(X) P(Y)P(Z) we need to first show that (e.g.) X⊥Y and that Z⊥Y|X; it is not sufficient. to show just that X⊥Y and X⊥Z and Y⊥Z. In fact, independence of random variables is such a strong condition, that the commonest error in Bayesian software is probably due to assuming that a set of random variables are independent when actually they are not.

Extension of the above arguments leads to many other fowls of the chain rule, for example telling us that for any events (or random variables) A, B, C, D, E we have $$P(A,B,C,D|E)=P(A|E)P(B|A,E)P(C|A,B,E)P(D|A,B,C,E)$$

with extensions to larger numbers of variables, or with omission of E throughout (if we are dealing with continuous random variables rather than events then there are technical restrictions that the various densities must exist).

1.1.4 Marginalisation Rule

Suppose we have two disjoint events (i.e. mutually exclusive events) $B_0$ and $B_1$ such that $P(B_0)+P(B_1)=1$; suppose also that for some event A we know both $P(A,B_0)$ and $P(A,B_1)$. Then the simplest form of the marginalisation rule tells us that $$P(A)=P(A,B_1)+P(A,B_2).$$

For two random variables A, B for which we know the joint probability distribution P(A,B), we may want to know the marginal distribution P(A). The marginalisation rule tells us that $$P(A)=\int P(A,B)dB$$

where the obvious interpretation of the formula is in terms of probability density functions. If the variables are discrete a corresponding summation of probabilities may be used, or a measure-theoretic integral with all the measure on the atoms of B; the latter possibility can easily generalise to handle the situation where the variables are partly discrete and partly continuous, for example, or of variable dimensionality (e.g. the coefficients of polynomials of unknown degree).

More generally, for a number of random variables A, B, C, D, E for example, the marginalisation rule tells us that $$P(A,B|E)=P(A,B,C,D|E)dCdD$$

(and many other obvious variants obtained by omitting some variables etc).

1.2 Bayes' Theorem

Let us suppose that θ represents what we want to know. Usually θ will be a vector of many numbers; it might for example be the vector of intensities of a number of fluors. Let us suppose that D represents what we do know. D might for example be the arrival times of some photons. Now, we know that for any specific value of θ, which specifies the vector of intensities, that some values of D are more likely and others less likely, and because we know the manner in which the data arises from θ, we can say exactly how much more or less likely. In other words, we can evaluate, for any specific values of θ and D, the value of P(D|θ), the probability of D given θ.

We also know, before we even receive D, that some values of θ are more likely than others. For the photon counting example negative intensities can be excluded, as can values of the intensities that are extremely large (e.g. >$10^{15}$ per second) or too small. This can all be precisely specified as a prior distribution on θ, denoted P(θ).

What we actually want to know is the value of θ, given some specific value of D.

This is given by Bayes' theorem:

$$P(\theta | D) = \frac{P(\theta)P(D | \theta)}{\int P(\theta)P(D | \theta)d\theta}$$

which tells us that given that particular value of D, just how likely each value of θ is. The parts of the above equation are named as follows:

| | |
|---|---|
| P(θ) | the Prior |
| P(D\|θ) | the Likelihood |
| P(θ\|D) | the Posterior |
| ∫ P(θ)P(D\|θ)dθ | the Evidence (for the model) |

1.3 Implications of Bayes' Theorem for Determining the Possibility or Impossibility of Various Problems Suppose now that we know some prior on $\theta$, the likelihood, and some value of D. Clearly we can calculate the value of the posterior for any $\theta$ (leaving aside computational difficulties for the moment). The question of interest now is, is it possible for any technique to produce a value of $\theta$, or a range of values of $\theta$, that is in any way better than the Bayesian posterior distribution? To get an approximate intuitive idea why the answer to this is No, let us consider an example problem where the true answer (known because the problem was synthesized, for example) is $\theta_0$, and the Bayesian posterior is $P(\theta|D)$, non-zero on values of $\theta$ other than $\theta_0$ (as well as on $\theta_0$). Suppose there is some other technique which comes up with the single value $\theta_0$ when fed with D. Then, while this produces a correct and unambiguous answer for this particular problem, there will in general be other similar problems which also produce the same data D, for which the true answer is not $\theta_0$. The technique must necessarily still produce the answer $\theta_0$ (since it has been fed the same data); but for these other problems this answer will be wrong. The Bayesian answer "hedges its bets" to precisely the right extent. If in fact there are no other values of $\theta$ that ever produce D, then it is easily verified that $P(\theta|D)$ will be non zero only for $\theta=\theta_0$, in which case both Bayes and the wonder technique give the same answer, so the wonder technique is not better, just the same.

1.4 What is the Best Way to Use the Posterior Distribution?

Let us now suppose that we have some formula giving the value of $P(\theta|D)$ for any value of $\theta$ (and remember here that $\theta$ is often a vector with many hundreds of components). This formula, as we have seen, hedges its bets on the value of $\theta$ to just the right extent. However, as an answer for a human being the formula is hopeless, as by itself it carries no intuition about which values of $\theta$ are likely and which are not.

1.4.1 The Options

We may consider a number of possible ways to use $P(\theta|D)$, as follows.

1.4.1.1 View the Entire Posterior Distribution

This is possible in some cases (dimensionality not more than 2 and calculations turn out reasonably easy), impossible in others. It is, however, almost never the computationally cheapest way to use Bayes.

1.4.1.2 MAP (Maximum a Posteriori)

Here we find the value of $\theta$ where the posterior probability density is greatest (if we can), and report just that value of $\theta$. This is the approach most commonly favoured by the uninitiated. In the particular case that the prior on $\theta$ is flat (i.e. that there is equal prior probability density at all values of $\theta$) this approach is equivalent to the familiar maximum likelihood approach. It is frequently difficult, however, to find the maximum of a posterior distribution of interest.

1.4.1.3 Mean Posterior Value

Alternatively we can report the mean posterior value of $\theta$, namely $\int \theta P(\theta|D) d\theta$. Again, this assumes that this integral is evaluable in some practically feasible way.

1.4.1.4 Random Samples

As our final option, we consider drawing random samples from the distribution $P(\theta|D)$.

1.4.2 Reasons for the Recommended Choice—Random Samples

In many problems random samples from the posterior are easier to obtain than the MAP value or the mean posterior value. That, however, is not the main reason for preferring them. To understand why the mean is not always a good idea, consider the distribution consisting of a mixture of two Gaussians, both of standard deviation 1, but with means at 10 and 100. The mean of this distribution is at 55—but this value is one that will virtually never be the correct answer.

To understand why random samples are superior to the MAP solution, we need to consider a simple example. The key idea behind this is that probability density is not probability.

Let us suppose that our unknown, $\theta$, is a 2-component vector, (x,y). Let us suppose that its posterior distribution is as illustrated in FIG. 12; it is (we suppose) a mixture of 2 spherical Gaussians, one of mean (−20, 0) and standard deviation 1, and one of mean (+20, 0) and standard deviation 10. Let us suppose moreover that the mixture is such that the height of the left hand peak is 10 times higher than that of the right hand peak. Let us also suppose that what we most want to know is whether x is positive or negative.

Consider the volume of the tall narrow peak, compared with the volume of the low broad peak; the latter is 10 times larger than the former. Consequently the probability is 0.91 that the true answer comes from the low broad peak, and only 0.09 that it comes from the tall narrow one. However, the MAP solution lies in the tall narrow one.

Figure 13:
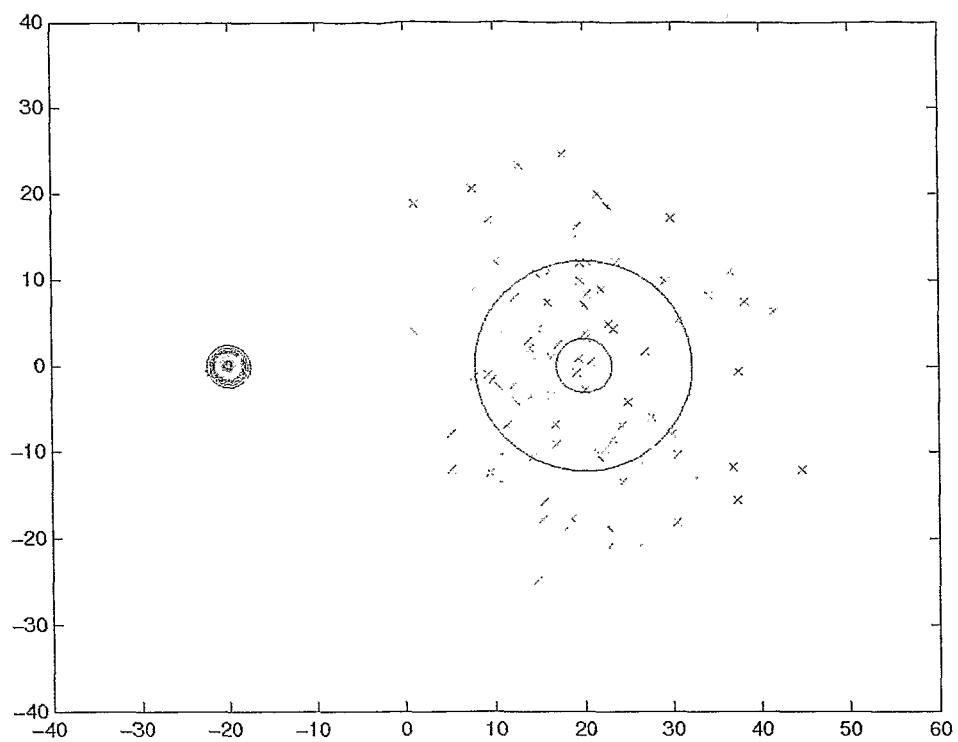
Figure 14:
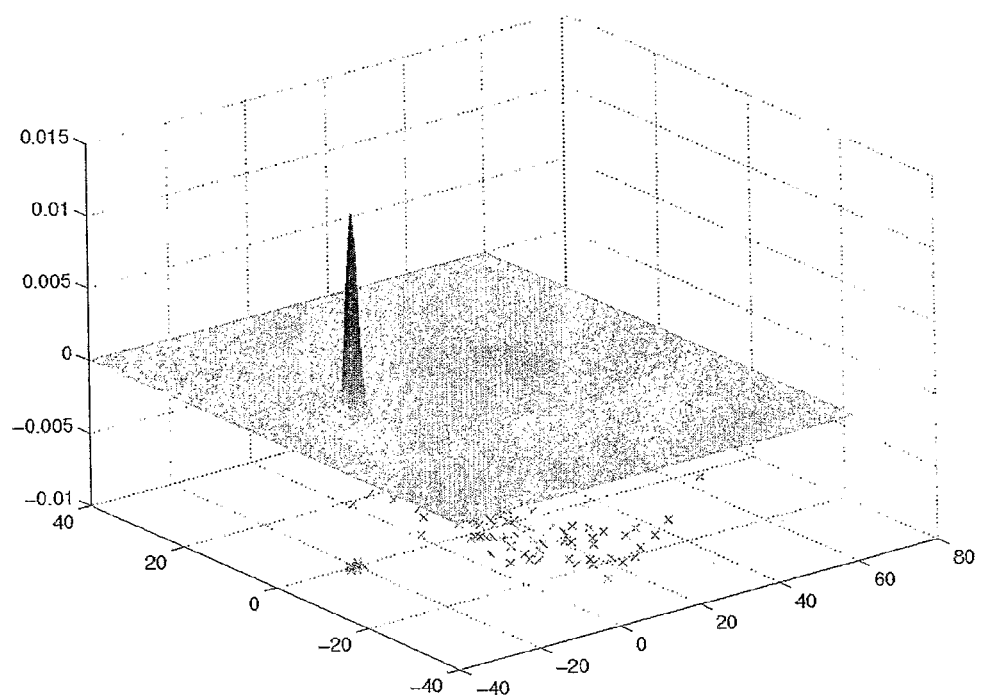

Now observe what happens when random samples are drawn from this 2-peaked distribution. FIG. 13 and FIG. 14 each illustrate the same 100 independent random samples from the distribution (viewed as a contour plot from below in FIG. 18). 90 of them are in the low broad peak, and 10 from the tall narrow one—vastly more representative than the MAP solution.

1.4.3 The "Joint" and the "Marginal" Distributions

Figure 15:
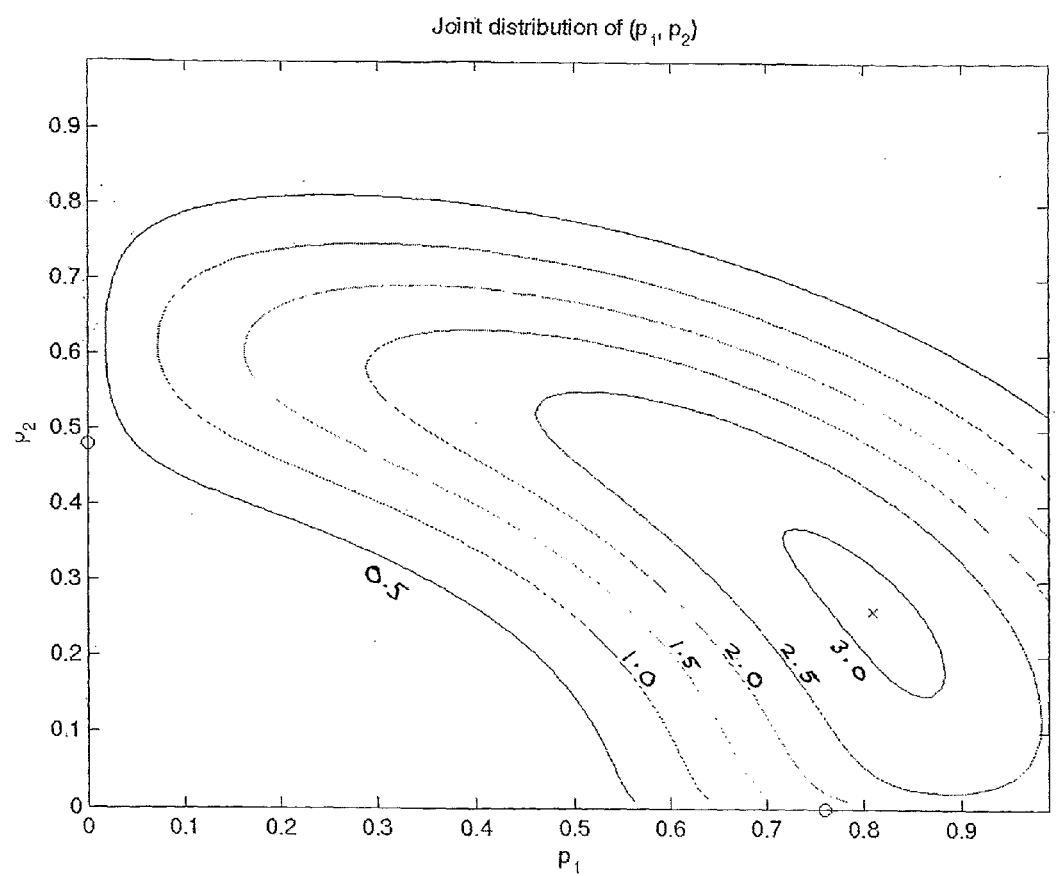
Figure 16:
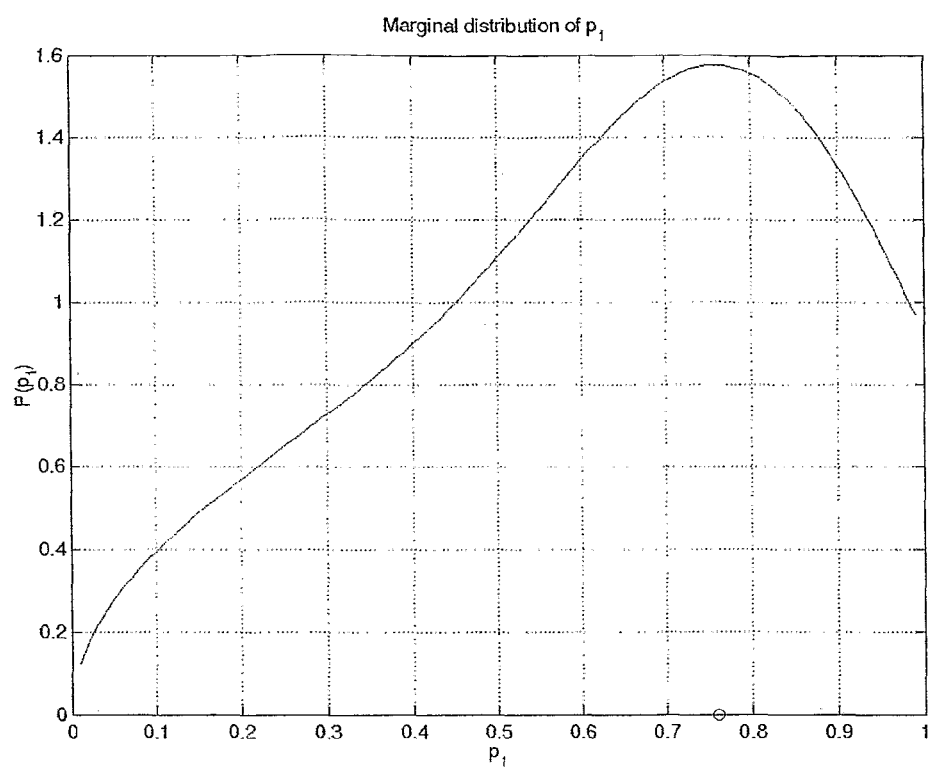
Figure 17:
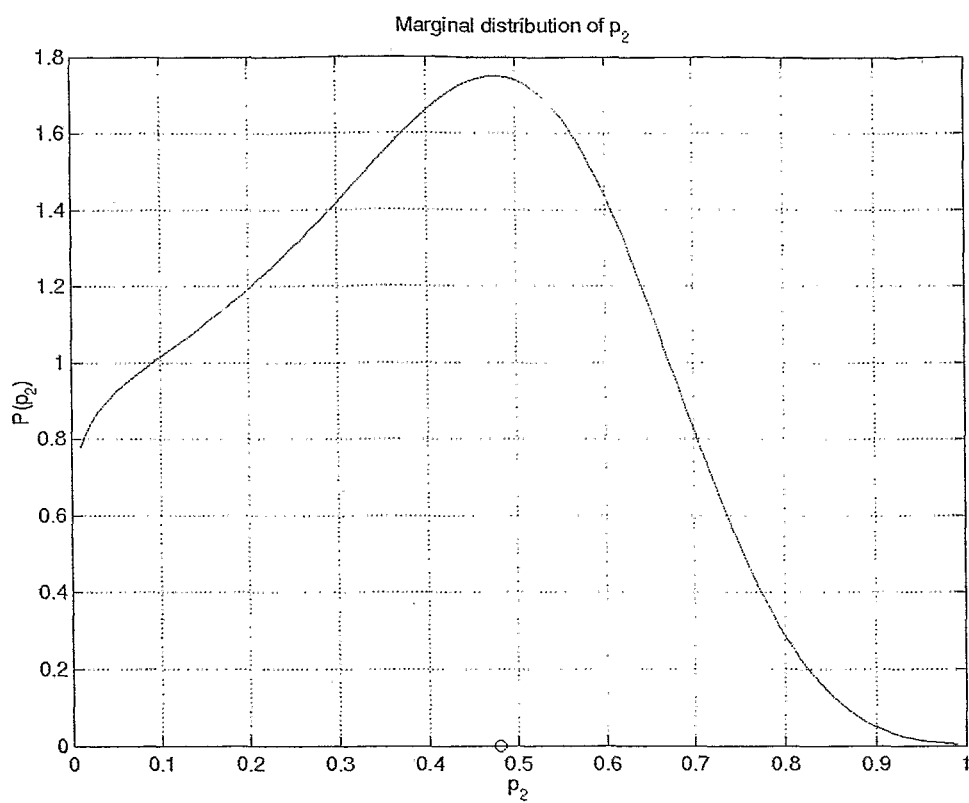

A further illustration of why random samples are superior to the MAP (or "posterior mode") value can be seen by considering the following 2-dimensional distribution (FIG. 15).

As can clearly be seen, the joint mode is not at the coordinates given by the two marginal modes (whose correct positioning can be seen both from the circles on the axes of 13 and from 14 and 15 below). Given only the joint mode (the MAP value of the joint posterior), we cannot deduce the MAP values of $p_1$ and $p_2$; but given samples of p (i.e. of $(p_1, p_2)$), we can throw away the second component of each sample and get a set of samples of $p_1$ for example.

What has happened is that to get the marginal probability densities, we have to integrate the joint probability density over the other dimensions; because the maximum value of the integral does not necessarily occur with the integrand with the maximum maximum (sic), the modes do not correspond.

1.4.4 Deductions on Particular Properties of the Solution

Usually, we are interested in more than just what the true answer might be—we are also interested in some derived properties of the solution; in the first example above we were interested in whether the x component of the solution was positive or negative. Such properties can be most realistically evaluated by looking at the relevant property of each of the posterior random samples. In the 2-D example of FIG. 13, we would deduce that the probability that the x component is positive is around 0.9 (indeed it was actually around 0.9) (Note that the MAP solution would suggest that the x component is always negative).

1.4.5 Using Non-independent Random Samples

Figure 18:
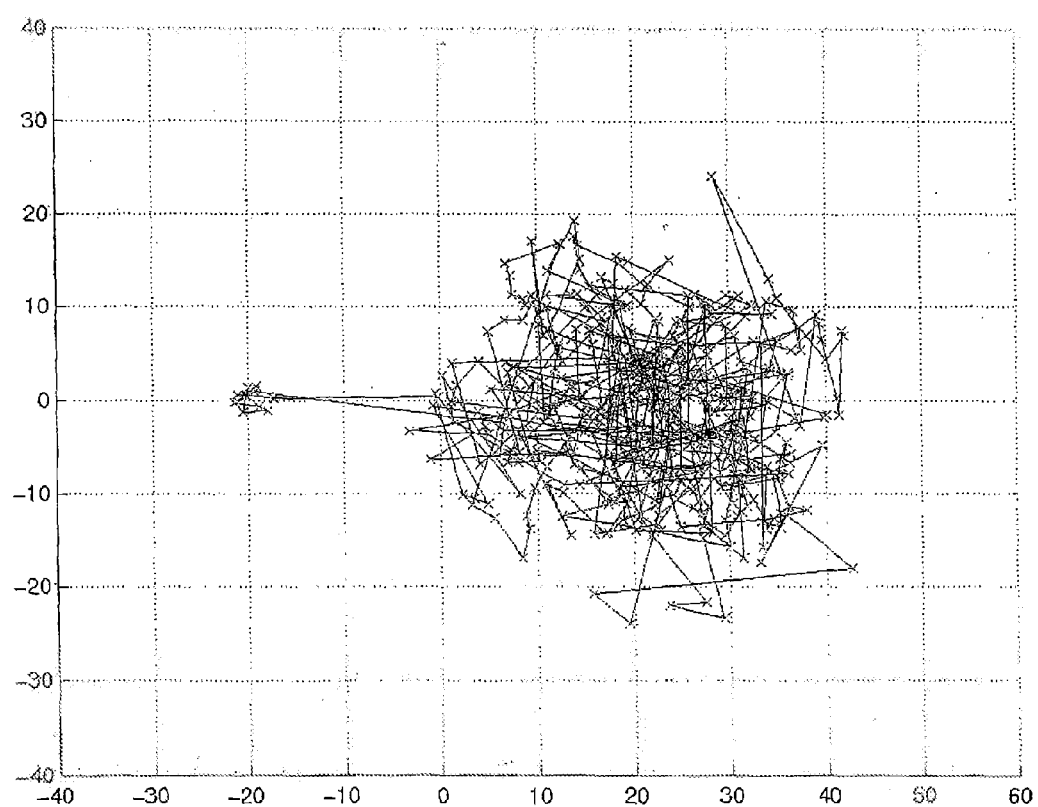

The samples drawn in FIG. 13 above were independent random samples. In real problems we are often unable to obtain independent random samples, and have to make do with dependent random samples. An illustration of how dependent random samples may behave is shown in FIG. 18 where now each sample has been joined by a line to the next sample following it.

We note here that each sample is more likely to be near its predecessor than would an independent sample; while this is the usual situation, in some circumstances one can obtain samples that are more likely to be far from their neighbours than independent samples would be. In this figure there are around 917 samples, but the number of distinct points on which samples lie is much lower than this (because most points have been sampled more than once in succession). In particular, 132 of the 917 samples come from within the contours of the tall narrow peak; yet they lie on only 12 distinct points. Thus despite using many more samples, the variance of the number lying in the left half-plane is a larger fraction of the total, due to the non-independence.

Now, suppose we are faced with not knowing whether it is possible to deduce from our data whether the true answer lies in the left half plane or the right half plane, in a situation where we actually know the true answer; suppose in this instance the true answer is (−20.3, 0.4), which is in the tall narrow peak in the left half plane. If we initialise such a dependent sampling process from the true answer, and it starts sampling from the opposite half plane (as it would in this instance), and a majority of the samples come from the right half plane, then we know that it is not possible to deduce the true answer from the data, as if we did we would usually be wrong.

Taking the opposite point of view, suppose instead the true answer is (23, 5). Now, wherever we start from, we end up sampling from the right half plane before long. The samples will mostly lie in the right half plane, but in a large region centred on (20, 0). This tells us that it is possible to deduce that the true answer is probably in the right half plane, but also that we cannot determine it to within a distance of 0.1, 1, or even 10.

This type of non-independent sampling is the type of technique on which the fast algorithms we discuss are based.

1.5 Markov Chain Monte-Carlo Sampling 1.5.1 General MCMC Methods

The question then arises: how do we obtain such random samples from a posterior distribution? In simple cases there are a variety of direct methods for taking random samples from a wide variety of relatively straightforward distributions; the easiest to understand is inversion, where a 1-dimensional distribution is sampled by picking a uniformly distributed random number p between 0 and 1, then setting the sample to be that value $x_0$ such that the probability $P(x < x_0) = p$. This approach yields nicely independent samples, but requires the cumulative probability function $P(x<x_0)$ and hence the ability to integrate the density—and that the resulting function can then be inverted to find the $x_0$ for any given p. Inversion can be extended to sampling multi-dimensional distributions $P(x)$ of a vector variable x by sampling first $x_1$ (the first component) from the marginal distribution $P(x_1)$, then sampling $x_2$ from the marginal conditional distribution $P(x_2|x_1)$, then $x_3$ from $P(x_3|x_1,x_2)$, etc. However for most posteriors of interest this hits computational intractability either immediately (difficulty calculating the first marginal distribution) or somewhere along the chain.

We therefore often turn to Markov chain Monte-Carlo sampling (abbreviated to MCMC). This produces a sequence of randomly chosen values of x, say $x_1, x_2, \ldots$ such that each is dependent on the one before (and independent of its other predecessors given its immediate predecessor), and such that no matter what the value of $x_n$, we can be sure that for sufficiently large values of k, $x_{n+k}$ will be distributed both independently of $x_n$ and according to the desired distribution $P(x)$; moreover if $x_n$ is distributed according to $P(x)$, so will $x_{n+1}$ be.

Let us suppose that $P(x)=Kf(x)$ for some unknown constant $K>0$, where the function $f$ is known. Then we must ask: what are the requirements on a rule for choosing $x_{n+1}$, given $x_n$, such that we do indeed get samples from $P(x)$ as described above? It turns out to be sufficient that two conditions hold, known as "detailed balance" and "reachability".

Detailed balance requires that for any two values of $x_n$, say $x_{n,1}$ and $x_{n,2}$, we have $f(x_{n,1})P(x_{n+1}=x_{n,2}|x_n=x_{n,1})=f(x_{n,2})P(x_{n+1}=x_{n,1}|x_n=x_{n,2})$; intuitively this means that the chance of being in one place to start with under the desired distribution and ending up in the other must be the same as the chance of being in the other place to start with under the desired distribution, and ending up in the one.

Reachability requires that there is some $\epsilon>0$ and some positive integer N such that for any two values x and x' and any positive integer n, we have $P(x_{x+N}=x'|x_n=x)\geq\epsilon P(x')$. Intuitively this says (slightly more than) that if we start off anywhere, there should be at least some probability of getting to anywhere where the desired distribution is not zero.

These are very weak conditions; consequently there are many many valid ways of setting up an MCMC process for any given desired distribution. The art of getting an MCMC process to be practically useful is to find a rule for updating $x_n$ that both meets detailed balance and reachability, and also is computationally feasible and runs fast enough to be practically useful.

1.5.2 Combining Methods that Achieve Detailed Balance

It turns out that we often need to combine two or more different ways of choosing the next sample in the chain; the usual reason is that each of the different ways of choosing the next sample meets detailed balance on its own, but none of them, on their own, meet the reachability condition. Our desire then is that some way of combining the different methods will lead to a method which meets both conditions.

Suppose then that we have L methods for choosing $x_{n+1}$ given $x_n$, say that method 1 draws $x_{n+1}$ from $P_1(x_{n+1}|x_n)$, a probability distribution for each $l\in\{1, 2, \ldots, L\}$, and that each of these methods satisfies the detailed balance criterion. Then one might be forgiven for thinking that applying each of the methods in turn, one after the other, would also satisfy detailed balance—but one would be wrong.

There are (at least) two ways of undertaking such a combination that do lead to an overall method that satisfies detailed balance. The first is to combine the different methods palindromically, and the second is to combine them randomly.

Combining the methods palindromically involves the following steps. First we draw $x_{n+1}$ from $P_1(x_{n+1}|x_n)$; then draw $x_{n+2}$ from $P_2(x_{n+2}|x_{n+1})$; then . . . ; then draw $x_{n+L}$ from $P_L(x_{n+L}|x_{n+L-1})$; then draw $x_{n+L+1}$ from $P_{L-1}(x_{n+L+1}|x_{n+L})$; then draw $x_{n+L+2}$ from $P_{L-2}(x_{n+L+2}|x_{n+L+1})$; then draw . . . ; then draw $x_{n+L+L-1}$ from $P_1(x_{n+L+L-1}|x_{n+L+L-2})$. The overall method, which amounts to drawing $x_{n+2L-1}$ given $x_n$ from some resulting distribution $P(x_{n+2L-1}|x_n)$, then also satisfies detailed balance. If we have chosen the $P_l$ suitably, we may also be lucky and find that it also satisfies the reachability criterion.

On the other hand combining the methods randomly uses the following sequence of steps: first draw l at random from some fixed distribution (which must be specified) on $\{1, 2, \ldots, L\}$, then use method l by itself to obtain $x_{n+1}$ by drawing $x_{n+1}$ from $P_l(x_{n+1}|x_n)$. The resulting method of obtaining $x_{n+1}$ from $x_n$ then satisfies detailed balance, and if we have chosen the $P_l$ suitably, we may also be lucky and find that it also satisfies the reachability criterion.

1.5.3 Gibbs Sampling

Gibbs sampling is one particular type of MCMC method that involves combining a number of simple methods into an overall grand method using either of the methods of combination described in 1.5.2 above; it works in principle using either palindromic or random combination, and it is a matter of experiment to determine which produces faster running in practice.

To understand Gibbs sampling we will suppose that our vector variable x is three dimensional, and we will denote the three dimensions by separate letters, so that $$x = \begin{pmatrix} x \\ y \\ z \end{pmatrix}.$$

Suppose now that we have $$x_n = \begin{pmatrix} x_n \\ y_n \\ z_n \end{pmatrix},$$

then: method 1 consists of drawing $x_{n+1}$ from $P(x_{n+1}|y_n,z_n)$ and setting $y_{n+1}=y_n$, $z_{n+1}=z_n$; method 2 consists of drawing $y_{n+1}$ from $P(y_{n+1}|x_n,z_n)$ and setting $x_{n+1}=x_n$, $z_{n+1}=z_n$; and method 3 consists of drawing $z_{n+1}$ from $P(z_{n+1}|x_n,y_n)$ and setting $x_{n+1}=x_n$, $y_{n+1}=y_n$. All three methods then finish by combining the separate (coordinate) variables into the resulting vector $$x_{n+1} = \begin{pmatrix} x_{n+1} \\ y_{n+1} \\ z_{n+1} \end{pmatrix}.$$

It should then be clear that method 1, while it meets the detailed balance criterion, has no hope of meeting the reachability criterion—it never changes the y or z coordinates of the point where we already were (and similarly for the other two methods). However if we combine the three methods (whether palindromically or randomly) we obtain a method which achieves detailed balance and may achieve reachability also (whether it does or not depends on further information about the distribution P(x) from which we are trying to sample).

One should note that doing Gibbs sampling depends on being able to sample from the conditional distributions (e.g. P(x|y,z)). Further, any coordinate transformation (for example to cylindrical coordinates, or even just to a rotated set of Cartesian coordinates) will result both in a completely different set of conditional distributions, and in an algorithm that may be many orders of magnitude better or worse than the one you started with. So again, Gibbs sampling is a framework for designing an algorithm, but one which still requires art and skill to implement it.

1.5.4 Variations on Gibbs Sampling

It is frequently the case, including in this present invention, that one wants to use a method that resembles Gibbs sampling but in which one (or more) of the (in the example three) simple steps is replaced by a more complicated step that changes only the one coordinate (or one subset of the coordinates) but which meets detailed balance. It should be clear from the above that if that more complicated step meets reachability with respect to the relevant conditional distribution (e.g. P(x|y, z)) then the result will be a combined method that has just as good a chance of meeting both the necessary conditions as would Gibbs sampling (and which may be practical in some situations in which the corresponding Gibbs sampling sub-parts are impractical).

1.5.5 The Metropolis-Hastings Algorithm

We want to sample from some distribution $P(x)=Kf(x)$ for some unknown constant $K>0$, where the function $f$ is known. However it is difficult to sample from $f(x)$, so we would prefer to find some way of sampling from some other distribution and then somehow correcting for the difference. Let us then think of some other distribution $g(x|x_n)$ (known as the proposal distribution, parameterised by $x_n$) from which we can sample somehow, and suppose that we have just issued sample $x_n$. To issue sample $x_{n+1}$ we proceed as follows. First, we draw a sample x from $g(x|x_n)$. Second, we calculate a number q, known as the Hastings ratio, according to $$q = \frac{f(x)g(x_n | x)}{f(x_n)g(x | x_n)}.$$

Third, we draw a random number u from the uniform distribution on the interval [0,1]. Finally, if u≤q we set $x_{n+1}=x$, while otherwise we set $x_{n+1}=x_n$.

This results in a way of producing $x_{n+1}$ that adheres to detailed balance, as is easily shown. Therefore, if used in a way (perhaps in combination with other types of move as described in 1.5.2) that also satisfies the reachability criterion, it results in a method of drawing non-independent random samples from a distribution that converges to the desired distribution. However, it does not necessarily converge rapidly; indeed if $g(x|x_n)$ bears little relationship to $f(x)$, it will take a very long time to do so (as $x_{n+1}$ will usually be identical to $x_n$, and on the rare occasions when it is not it will be very close to $x_n$). Therefore use of Metropolis-Hastings moves does not in any way absolve the designer from using his art and skill to design appropriate proposal distributions to make the method work well.

1.5.6 Simulated Annealing

It turns out that we often need to use further devices to speed up convergence of MCMC sampling schemes. One of the important ones is the following, known as simulated annealing because it originally drew its inspiration from allowing metals to cool slowly and repeatedly from the molten state in order to obtain a better crystalline structure for the final solid metal. Accordingly the variable κ in the following, which can be thought of as the reciprocal of temperature, is known as the "coolness".

Suppose then that we want to sample from the distribution $P_1(x)$, and have designed a sampling scheme that achieves this, but too slowly for practical use. Suppose we also have a scheme that achieves sampling from some other distribution $P_0(x)$ and converges rapidly (or even immediately). Suppose further that $P_0(x)=0 \to P_1(x)=0$, i.e. that anywhere that $P_0(x)$ is zero $P_1(x)$ is also zero. Then we proceed in the following manner. We construct a sequence of values of κ stepping slowly from 0 to 1, i.e. $0=\kappa_0<\kappa_1<\kappa_2<\ldots<\kappa_K=1$. Define $P_{\kappa_k}(x)=(P_0(x))^{1-\kappa_k}(P_1(x))^{\kappa_k}$. Then we start by using our rapid sampling scheme for $P_0$ to draw $x_0$. Then we apply an MCMC move that satisfies detailed balance not with respect to $P_1$ but to $P_{\kappa_1}$ to give us the next sample $x_1$. So long as k<K we get $x_k$ from $x_{k-1}$ by applying an MCMC move that satisfies detailed balance with respect to $P_{\kappa_k}$. Thereafter we get $x_k$ from $x_{k-1}$ by applying MCMC moves that satisfy detailed balance with respect to $P_1$.

The end result is usually that our overall MCMC sampling scheme converges faster than it would if we just started from some random value for $x_0$ and then applied MCMC moves satisfying detailed balance with respect to $P_1$. However, ensuring that this is so, and choosing the correct initial distribution $P_0$ and sequence of $\kappa_k$, forms part of the art and skill of the designer.

1.6 Analytic Options

The above MCMC techniques can be got to work on almost all problems to which one wants to apply Bayes (though there is no guarantee on how fast). However, there are many problems where an analytic route to obtaining independent random samples is possible and preferable, or where part of the implementation of an MCMC system can be made to work very much faster by doing part of the problem analytically. If one is dealing with a monomodal posterior distribution it may also be possible and useful to find the MAP or mean posterior value analytically. Whichever of these situations applies, in order that analytic techniques can be used, it is usually necessary to deliberately set the problem up in a way which will be conducive to an analytic (or part-analytic) solution. The key idea here is that of 'conjugate priors'.

1.6.1 Conjugate Priors

Given a likelihood $P(D|\theta)$ for general D, which will always be a probability distribution in D for any fixed value of $\theta$, it may be the case that it is also a multiple of a probability distribution in $\theta$ for each fixed value of D, and even that products of such likelihoods are also multiples of valid probability distributions in $\theta$.

If so, then we can consider setting up our Bayesian inference using prior distributions which take the same generic form as the likelihood function relevant to the problem expressed as functions of $\theta$. This will usually result in the product of the prior and the likelihood taking a form that is analytically integrable, and hence in an exact analytic expression for the posterior as well as for the evidence for the model.

Well known examples of likelihoods for which this occurs are the Gaussian likelihood (giving us a conjugate prior Gaussian distribution for the mean or alternatively a conjugate Wishart prior distribution for the scale matrix), the Poisson likelihood (giving us a conjugate Gamma distribution for the rate parameter), and the Multinomial likelihood (giving us a conjugate Dirichlet distribution for the probability vector parameter).

1.6.2 Reasons to Use Conjugate Prior Distributions

We have already seen that conjugate priors result in advantages in terms of analytic tractability of the mathematics. However, that by itself is insufficient reason to use them. There are however two other powerful reasons why conjugate priors may be appropriate for many problems.

The first is that if the data on which the prior is based is of the same nature as the data for the problem in question, and if one originally had a nearly-flat prior distribution in $\theta$, then the true prior will indeed approximately belong to the conjugate family. The second is that most families of conjugate priors are capable of expressing the prior beliefs relevant to a very wide range of problems. There are of course exceptions; the most frequently seen is that where the likelihood is Gaussian (and the conjugate prior for the mean therefore also Gaussian) but the prior knowledge tells us that $\theta$ is positive with probability 1, a situation that usually cannot be reasonably approximated by a Gaussian distribution—in fact precisely this circumstance occurs in part of the present invention, while useful conjugate distributions are used elsewhere in it.

1.7 Hierarchical Models

It is now necessary to examine how one builds up complex models from simple ones. It is easiest to communicate this by examining a simple example.

Moreover the example differs from the present invention in that it is largely analytically tractable without using sampling techniques; this means both that it is simpler (in that it does not use sampling) but also more complicated (more analytic maths to be worked through). It is present for the purpose of showing what can be done without sampling and to aid understanding of the non-sampling parts of the present invention.

Suppose that we are observing two populations of monkeys—say Talls and Shorts (indicating their race rather than their actual individual heights). The observations we obtain consist of the weight of an individual, and from that observation we wish to deduce whether the individual belongs to the Tall or the Short race/species. Since Talls and Shorts both suffer from the usual range of physiques, from anorexic to obese, the problem is not necessarily trivial.

Let us suppose moreover that we believe that, within a racial group, weight is log-normally distributed; we may however not know either mean or standard deviation of either distribution. In addition we do not know what fraction p of the population is of the Tall race, but we have some prior beliefs that it is roughly 2 Tall to every 1 Short. How then do we put a model together that expresses this information?

Let us denote race by a 0/1 variable R (1 meaning Tall), and the race of particular individual i by $R_i$. Let $\sigma_R$ and $\mu_R$ denote the standard deviation and mean of log weight of individuals of race R, and let $$s_R = \frac{1}{\sigma_R^2} \cdot \mu, \sigma, s$$

without subscripts will denote the vectors consisting of e.g. $\mu_0$ and $\mu_1$. Let $w_i$ denote the log weight of individual i (weight (really meaning mass here) being always measured in kg). We might start by specifying the distribution of $w_i$ given the other parameters; we might then have wondered "What values should I set for $\mu_0$ and $\mu_1$?". Since we don't know the values of $\mu_0$ and $\mu_1$, we then have to specify a prior distribution for these variables; similarly for $\sigma_0$ and $\sigma_1$, and for the value of p. This leads to a hierarchy of equations which specify our model. Choosing/designing these equations to both reflect our beliefs and also lead to a tractable problem is of course a skill or art-form.

Having done that, the information above could for example be expressed mathematically by the following set of equations; the precise equations used will reflect our beliefs before seeing any data. The equations are listed in logical order, rather than in the order in which they have been presented above.

| | |
|---|---|
| $P(p) = \frac{\Gamma(9)}{\Gamma(6)\Gamma(3)} p^5 (1-p)^2$ (Beta distribution with parameters 6 and 3) | This tells us that p is distributed corresponding to our prior beliefs that their are probably more Talls in the population. |
| $P(R_i \mid p) = p^{R_i}(1-p)^{1-R_i}$ | This tells us what p means. |

-continued $P(\mu_R \mid R) = P(\mu_R \mid R, p, \mu_{1-R})$ $= \sqrt{\dfrac{1}{2\pi}} e^{-\frac{1}{2}(\mu_R - 3^R 2^{(1-R)})^2}$ (Gaussian distribution with mean dependent on R and standard deviation of 1 neper)

This tells us that we think that the Talls are likely to weigh more than the Shorts, and that we have wide priors on the values of $\mu_0$ and $\mu_1$.

$P(s_R \mid R) = P(s_R \mid R, \mu, s_{1-R}, p)$ $= \dfrac{5^5}{\Gamma(5)} s_R^4 e^{-5 s_R}$ (Gamma distribution with shape 5 and mean 1)

This tells us that $\sigma_R$ is distributed so that we are fairly sure it will not be less than 0.3 nepers, is most likely to be about 0.5 nepers, but could be quite a bit bigger. It also tells us that $\sigma_0$ and $\sigma_1$ are identically and independently distributed in our prior.

$P(w_i \mid R_i, \mu_{R_i}, s_{R_i}) = P(w_i \mid R_i, \mu, s, p)$ $= \sqrt{\dfrac{s_{R_i}}{2\pi}} e^{-\frac{s_{R_i}}{2}(w_i - \mu_{R_i})^2}$ (Gaussian distribution with mean and standard deviation potentially dependent on R)

This tells us how an individuals log-weight is distributed given the values of the parameters.

$i \neq j \Rightarrow w_i \perp w_j \mid R_i, R_j, \mu, s, p$
(Statement of independence to resolve doubt)

This tells us that $w_i$ and $w_j$ are independently distributed given all the parameters (as was actually already implied by the preceding equations).

What we have done here is to build a total model up out of a number of parts, in a so-called "hierarchy". It is worth reflecting for a moment on how many equations have arisen for this very simple problem, and why they are necessary. There are of course many ways we could set up a simpler set of equations by having more precise prior knowledge, but here our purpose is to illustrate what to do when our prior knowledge is relatively imprecise.

The question now is how we combine all these equations and reach an appropriate analysis of the problem.

We will consider two variants of the problem: that where there is some data on a random sample of the overall population, and where there is not. For both we have the log weight $w_0$ of some individual to be classified. Where there is training data it consists of $\{(w_i, R_i) : i \in I\}$ for some indexing set I which does not contain 0.

We will assume training data is available first; the case without training data is then just the simplification that $I = \emptyset$. If the reader is interested purely in the present patent specification then he may like to note that that falls within the case that no training data is available.

1.7.1 Training Data Available

Let w and R (without subscripts) denote $(w_i)_{i \in I}$ and $(R_i)_{i \in I}$ respectively. Then what we want to know is $P(R_0 \mid w_0, w, R)$, which tells us how probable it is, in the light of all the data, that the new individual belongs to race $R_0$. Using Bayes' theorem we arrive at the following series of equations (where all integrals are over the entire possible range of the variable of integration, and where the "is proportional to" symbol $\propto$ means that the constant of proportionality does not vary with $R_0$):

$P(R_0 \mid w_0, w, R) = \int P(R_0, p \mid w_0, w, R) dp$ (marginalisation rule)

$= \int \dfrac{P(R_0, p) P(w_0, w, R \mid R_0, p)}{\int P(R_0, p) P(w_0, w, R \mid R_0, p) d(p, R_0)} dp$ (Bayes' theorem)

-continued $\propto \int P(R_0, p) P(w_0, w, R \mid R_0, p) dp$ (denominator invariant with $R_0$, p)

$= \int P(p) P(R_0 \mid p) P(w_0, w, R \mid R_0, p) dp$ (chain rule)

$= \int P(p) P(R_0 \mid p) P(w_0, w, R, s, \mu \mid R_0, p) d$ $(p, s, \mu)$ (marginalisation)

$= \int P(p) P(R_0 \mid p) P(R \mid p) P(s) P(\mu)$ $P(w \mid R, s, \mu) P(w_0 \mid R_0, s_{R_0}, \mu_{R_0}) d(p, s, \mu)$ where in the last line we have used the chain rule, followed by the conditional independences of:

R from $R_0$ given p (since $0 \notin I$)
s from p,R,$R_0$
$\mu$ from p,R,$R_0$,s
w from p,$R_0$ given R,s,$\mu$
$w_0$ from p,R,$s_{1-R_0}$,$\mu_{1-R_0}$ given $R_0$,$s_{R_0}$,$\mu_{R_0}$.

Note that it is not totally trivial to see which independencies are valid and which are not.

We can now proceed using the independences of the $w_i$ from each other given all the other parameters (see the text below the equations for help):

$P(R_0 \mid w_0, w, R) \propto \int P(p) P(R_0 \mid p) P(R \mid p)$ $P(s) P(\mu) P(w \mid R, s, \mu) P(w_0 \mid R_0, s_{R_0}, \mu_{R_0}) d(p, s, \mu) =$ $\int P(p) P(R_0 \mid p) P(R \mid p) P(s) P(\mu) \left( \prod_{R' \in \{0,1\}} \prod_{i \in I_{R'}} P(w_i \mid R_i, s_{R'}, \mu_{R'}) \right)$ $$P(w_0 \mid R_0, s_{R_0}, \mu_{R_0}) d(p, s, \mu) \propto \int P(p) p^{R_0+|I_1|} (1-p)^{1-R_0+|I_0|}$$

$$\left( \prod_{R' \in \{0,1\}} \left( P(s_{R'}) P(\mu_{R'}) \prod_{i \in I_{R'}} P(w_i \mid R_i, s_{R'}, \mu_{R'}) \right) \right)$$

$$P(w_0 \mid R_0, s_{R_0}, \mu_{R_0}) d(p, s, \mu)$$

where again we have used the independences of the components of s,μ from each other, as well as the equation defining the meaning of p, and where $I_j = \{i \in I : R_i = j\}$.

The next step is to substitute the expressions for the remaining probabilities and integrate over s.

Now, let $$I'_{R'} = \begin{cases} I_{R'} \cup \{0\} & (R' = R_0) \\ I_{R'} & (R' \neq R_0). \end{cases}$$

Then:

$$\int \prod_{R' \in \{0,1\}} \left( P(s_{R'}) \prod_{i \in I_{R'}} P(w_i \mid R_i, s_{R'}, \mu_{R'}) \right) P(w_0 \mid R_0, s_{R_0}, \mu_{R_0}) d(s_0, s_1) =$$

$$\prod_{R' \in \{0,1\}} \int P(s_{R'}) \prod_{i \in I'_{R'}} P(w_i \mid R_i, s_{R'}, \mu_{R'}) ds_{R'} \propto$$

$$\prod_{R' \in \{0,1\}} \int \left( \frac{s_{R'}}{2\pi} \right)^{4+|I'_{R'}|/2} e^{-\frac{s_{R'}}{2} \left( 5 + \frac{1}{2} \sum_{i \in I'_{R'}} (w_i - \mu_{R'})^2 \right)} ds_{R'} =$$

$$\prod_{R' \in \{0,1\}} (2\pi)^{-|I'_{R'}|/2} \frac{\Gamma(5 + |I'_{R'}|/2)}{\left( 5 + \frac{1}{2} \sum_{i \in I'_{R'}} (w_i - \mu_{R'})^2 \right)^{5+|I'_{R'}|/2}}$$

Therefore, substituting into the previous equations, we have $$P(R_0 \mid w_0, w, R) \propto \int P(p) p^{R_0+|I_1|} (1-p)^{1-R_0+|I_0|}$$

$$\left( \prod_{R' \in \{0,1\}} \left( P(s_{R'}) P(\mu_{R'}) \prod_{i \in I_{R'}} P(w_i \mid R_i, s_{R'}, \mu_{R'}) \right) \right)$$

$$P(w_0 \mid R_0, s_{R_0}, \mu_{R_0}) d(p, s, \mu) \propto \int p^{5+R_0+|I_1|} (1-p)^{3-R_0+|I_0|}$$

$$\left( \prod_{R' \in \{0,1\}} \frac{P(\mu_{R'})}{(2\pi)^{|I'_{R'}|/2}} \frac{\Gamma(5 + |I'_{R'}|/2)}{\left( 5 + \frac{1}{2} \sum_{i \in I'_{R'}} (w_i - \mu_{R'})^2 \right)^{5+|I'_{R'}|/2}} \right) d(p, \mu) \propto$$

$$\int p^{5+R_0+|I_1|} (1-p)^{3-R_0+|I_0|}$$

$$\left( \prod_{R' \in \{0,1\}} \frac{e^{-\frac{1}{2}(\mu_{R'} - 3^{R'} 2^{(1-R')})^2}}{(2\pi)^{|I'_{R'}|/2}} \frac{\Gamma(5 + |I'_{R'}|/2)}{\left( 5 + \frac{1}{2} \sum_{i \in I'_{R'}} (w_i - \mu_{R'})^2 \right)^{5+|I'_{R'}|/2}} \right)$$

$$d(p, \mu) = \int \frac{\Gamma(6+R_0+|I_1|)\Gamma(4-R_0+|I_0|)}{\Gamma(10+|I|)}$$

$$\left( \prod_{R' \in \{0,1\}} \frac{e^{-\frac{1}{2}(\mu_{R'} - 3^{R'} 2^{(1-R')})^2}}{(2\pi)^{|I'_{R'}|/2}} \frac{\Gamma(5 + |I'_{R'}|/2)}{\left( 5 + \frac{1}{2} \sum_{i \in I'_{R'}} (w_i - \mu_{R'})^2 \right)^{5+|I'_{R'}|/2}} \right) d\mu =$$

$$\frac{\Gamma(6+R_0+|I_1|)\Gamma(4-R_0+|I_0|)}{\Gamma(10+|I|)}$$

$$\prod_{R' \in \{0,1\}} \int \frac{e^{-\frac{1}{2}(\mu_{R'} - 3^{R'} 2^{(1-R')})^2} \Gamma(5 + |I'_{R'}|/2)}{\left( 5 + \frac{1}{2} \sum_{i \in I'_{R'}} (w_i - \mu_{R'})^2 \right)^{5+|I'_{R'}|/2}} d\mu_{R'}$$

which although it is believed is not analytically tractable, is only a product of two 1-dimensional integrals (one for each value of R') which are easy to evaluate numerically, once for each possible value of $R_0$.

1.7.2 No Training Data

The above expression then simplifies to:

$$P(R_0 \mid w_0) \propto \frac{\Gamma(6+R_0)\Gamma(4-R_0)}{\Gamma(10)}$$

$$\prod_{R' \in \{0,1\}} \int e^{-\frac{1}{2}(\mu_{R'} - 3^{R'} 2^{(1-R')})^2} \frac{\Gamma(5 + |I'_{R'}|/2)}{\left( 5 + \frac{1}{2} \sum_{i \in I'_{R'}} (w_i - \mu_{R'})^2 \right)^{5+|I'_{R'}|/2}} d\mu_{R'} \propto$$

$$\begin{cases} \Gamma(6)\Gamma(4) \int \frac{e^{-\frac{1}{2}(\mu_0 - 2)^2}}{\left( 5 + \frac{1}{2}(w_0 - \mu_0)^2 \right)^{5\frac{1}{2}}} d\mu_0 & (R_0 = 0) \\ \Gamma(7)\Gamma(3) \int \frac{e^{-\frac{1}{2}(\mu_1 - 3)^2}}{\left( 5 + \frac{1}{2}(w_0 - \mu_1)^2 \right)^{5\frac{1}{2}}} d\mu_1 & (R_0 = 1) \end{cases}$$

which is even easier.

1.7.3 Limitations of Alternative Methods in the Context of the Bayesian Solution If we had known nothing about Bayesian inference, one approach to the above problem, given training data, would have been to estimate the mean of each population by averaging the relevant part of the training data, to assume that each population had equal standard deviation, and to say that if the test individual's weight is nearer to one estimated mean than the other then we should classify him as such.

That would of course be a good first approximation to an answer—and it might well be good enough for a particular purpose. But it will certainly fall down if the training data does not contain any Talls, or (worse) if there is no training data, and it will never indicate any sort of probability of being right or wrong. It will also not take into account any of the information we know beforehand, while Bayes will precisely combine the prior knowledge and the effects of the new data.

The purpose of the above analysis is to show how the best possible inference can be made—and there will be some times when that is an appropriate thing to do, and others where the rough and ready guesstimate will do. In general it is appropriate to use Bayes where simpler methods have been shown not to be good enough, or where it is very easy to apply Bayes (as in fact it is in this case). One should consider the value of an optimal solution and the cost of obtaining it, and reach a balanced judgment.

1.8 Important Relevant Distributions and their Properties

In the above description we touched transiently on Gaussian and Gamma distributions. These and others are highly relevant to the present invention, and we therefore mention each briefly by way of introduction.

1.8.1 1-d Gaussian

This is the well-known "Normal" distribution on a 1-dimensional real variable. The density function is $$P(x \mid \mu, \sigma) = \frac{1}{\sigma\sqrt{2\pi}} e^{-\frac{1}{2}\left(\frac{x-\mu}{\sigma}\right)^2},$$

where $\mu$ is the mean and $\sigma > 0$ the standard deviation. Drawing a random sample from the 1-dimensional Gaussian distribution of zero mean and unit standard-deviation is done by drawing two random numbers $\mu_1, \mu_2$ independently from the uniform distribution on the open interval $(0,1)$, then calculating $x = \cos(2\pi u_1)\sqrt{2\log(u_2)}$. If a second (independent) sample from the same distribution happens to be needed at the same time it can be calculated as $x = \sin(2\pi u_1)\sqrt{2\log(u_2)}$.

Drawing a random sample from the 1-dimensional Gaussian with mean $\mu$ and standard deviation $\sigma$ is achieved by drawing one from the zero mean unit standard-deviation version then multiplying by $\sigma$ and adding $\mu$.

1.8.2 N-dimensional Gaussian

This is the same sort of thing, but for an N-dimensional variable. $\mu$ is now an N-dimensional vector, while the role of $$\frac{1}{\sigma^2}$$

is taken by the scale matrix S, a symmetric and positive-definite matrix. (Positive definite means that all the eigenvalues are positive.) The density function is $$P(x \mid \mu, S) = \sqrt{\det\left(\frac{S}{2\pi}\right)} e^{-\frac{1}{2}(x-\mu)' S(x-\mu)}$$

where x' denotes the complex-conjugate transpose of x (the same as the transpose if x is real as it is here).

Drawing a random sample from this distribution is achieved by the following steps:

- Calculate the Cholesky decomposition C of S, i.e. an upper triangular matrix such that $S = C'C$.
- Draw N independent random samples from the 1-dimensional zero mean unit standard deviation Gaussian as indicated in section 1.8.1, and assemble them into a column vector y.
- Calculate $x = C^{-1}y + \mu$; x is then the desired random sample from the given N-dimensional Gaussian.

1.8.3 Log-Gaussian

In the 1-dimensional case this is also known as the "log-normal" distribution. In the N-dimensional case we denote the elements, or coordinates, of the vector quantity x distributed as $x_n$ for $n = 1, 2, \ldots, N$, and denote by $\log(x)$ the vector quantity w whose elements $w_n$ are given by $w_n = \log(x_n)$. The density function is then $$P(x \mid \mu, S) = \sqrt{\det\left(\frac{S}{2\pi}\right)} \left(\prod_{n=1}^{N} \frac{1}{x_n}\right) e^{-\frac{1}{2}(\log(x)-\mu)' S(\log(x)-\mu)},$$

where $\mu$ is now the vector of logarithms of the median (not mean) number of droplets per unit volume in each bin of droplet radius.

The log-Gaussian distribution may be sampled by drawing a sample x from the Gaussian distribution with the same parameters, then exponentiating each element (coordinate) of x, i.e. replacing $$\begin{pmatrix} x_1 \\ x_2 \\ \vdots \\ x_N \end{pmatrix} \text{ by } \begin{pmatrix} e^{x_1} \\ e^{x_2} \\ \vdots \\ e^{x_N} \end{pmatrix}.$$

1.8.4 Gamma

The importance of the Gamma distribution lies in its conjugacy to the parameter $$s = \frac{1}{\sigma^2}$$

of the 1-d Gaussian distribution (and, but not for this patent, to the parameter $\lambda$ of the Poisson distribution). It has two parameters, the shape parameter m, and the scale parameter r. Both must be positive, and the quantity that is Gamma distributed can only be positive. For $m = 1$ the Gamma distribution is a negative exponential distribution; for smaller m it has a peak at zero, while for larger m the density is zero at zero and has a peak at $$\frac{m-1}{r}.$$

The mean is always $m/r$, and the variance is $$\frac{m}{r^2}.$$

The density function is $$P(x \mid m, r) = \frac{r^m}{\Gamma(m)} x^{m-1} e^{-rx}.$$

The $\Phi^2$ distribution with k degrees of freedom is a special case of the Gamma distribution, with shape $k/2$ and scale $1/2$.

Obtaining random samples from the Gamma distribution is done by different methods depending on the value of m, but all have in common that they first draw from $$P(x \mid m, r = 1) = \frac{1}{\Gamma(m)} x^{m-1} e^{-x} = q_0(x),$$

say, and then divide by the desired value of r. To draw from the distribution $q_0$ we proceed as follows.

The simplest case is $m = 1$, when one simply draws a random number u uniformly distributed in the open interval $(0,1)$ then calculates $x = -\log(u)$.

The case $m < 1$ we omit as it is not relevant to this patent specification.

The case $m > 1$ is handled as follows:

First, setting $$c = 3\left(m - \frac{1}{4}\right)$$

we note that we can obtain a sample x from the distribution $$P(x) = \frac{c}{2(c + (x - m + 1)^2)^{\frac{3}{2}}} = q_1(x),$$

say, (an example of a Student distribution—see the last paragraph of section 1.8.6 below) by drawing a random variable v uniformly distributed in the open interval (−1,1) and calculating $$x = \frac{v\sqrt{c}}{\sqrt{1 - v^2}} + m - 1.$$

Second, we note that there exists a constant $$A = \frac{2\sqrt{3\left(m - \frac{1}{4}\right)}}{\Gamma(m)\left(\frac{e}{m-1}\right)^{m-1}} > 0$$

such that $Aq_1(x) \geq q_0(x)$ for all $x>0$.

Therefore, if we first draw x from $q_1(x)$, then draw a random number w uniformly distributed in the open interval (0,1), and then $$\left(\text{if } w > \frac{q_0(x)}{Aq_1(x)}\right)$$

go back to the beginning and start again drawing a new x from $q_1(x)$, or $$\left(\text{if } w \leq \frac{q_0(x)}{Aq_1(x)}\right)$$

output x (as our random sample from $q_0$), we have succeeded in drawing a random sample from $q_0$, albeit in time that is only almost surely finite and integer-exponentially distributed with time constant A iterations (so that it takes on average A iterations, where A depends on m and lies in the range 1.35 to 3.1, but there is no upper limit to the number of iterations it might take).

1.8.5 Wishart

Continuing the theme of conjugate distributions, and noting that the Gamma distribution was the distribution conjugate to the 1-d Gaussian distribution with respect to the scale parameter $$s = \frac{1}{\sigma^2},$$

we may ask what distribution is conjugate to the N-dimensional Gaussian with respect to the scale matrix S. The answer is the Wishart distribution, first found (for a different purpose) around 1928. It is a distribution on symmetric positive definite matrices. For the purpose of its definition, and of compatibility with the Gamma distribution, we will define a parameter $k=2m+N-1$ related to the shape parameter $m>0$ of the Gamma distribution, and a covariance matrix $V=2rI_N$ if the Wishart is to be spherically symmetric (but which may be any positive definite symmetric matrix otherwise). The density function is then given either by $$P(S \mid k, V, N) = \frac{\det(V)^{\frac{k}{2}}}{2^{\frac{Nk}{2}} \pi^{N(N-1)/4} \prod_{j=0}^{N-1} \Gamma\left(\frac{k-j}{2}\right)} \det(S)^{\frac{k-N-1}{2}} e^{-\frac{1}{2}\text{trace}(SV)}$$

(in which case the mean of the distribution is $kV^{-1}$, while if S is so distributed then $S^{-1}$ has mean $R/(m-1)$ where $m>1$, $R=V/2$ and is infinite if $0<m<1$) or by $$P(S \mid m, R, N) = \frac{\det(R)^{m+\frac{N-1}{2}}}{\pi^{N(N-1)/4} \prod_{j=0}^{N-1} \Gamma\left(m + \frac{j}{2}\right)} \det(S)^{m-1} e^{-\text{trace}(RS)}.$$

in which form its relationship to the Gamma distribution becomes somewhat more apparent.

For the purposes of the present exposition, the importance of the Wishart distribution lies in its use defining the multi-dimensional Student distribution.

1.8.6 Student

Suppose now that we have a Gaussianly distributed quantity, but do not know the standard deviation, or the scale matrix in the multidimensional case. Suppose moreover that we use a conjugate prior on the scale matrix (sticking to the multidimensional case, since it is easily simplified later to the 1-d case), and that any data we have about the scale comes from samples of the Gaussian distribution concerned. The scale matrix is then Wishart distributed.

Some omitted mathematics then allows one to draw the following conclusions:

$$P(x \mid \mu, S, N) = \sqrt{\det\left(\frac{S}{2\pi}\right)} e^{-\frac{1}{2}(x-\mu)'S(x-\mu)}$$

$$P(S \mid k, V, N) = \frac{\det(V)^{\frac{k}{2}}}{2^{Nk/2} \pi^{N(N-1)/4} \prod_{j=0}^{N-1} \Gamma\left(\frac{k-j}{2}\right)} \det(S)^{\frac{k-N-1}{2}} e^{-\frac{1}{2}\text{trace}(SV)}$$

$$\therefore P(x \mid \mu, k, V, N) = \frac{\Gamma\left(m + \frac{N}{2}\right)}{\pi^{\frac{N}{2}} \Gamma(m)} \frac{\det(V)^{\frac{k}{2}}}{\det(V + (x-\mu)(x-\mu)')^{m+\frac{N}{2}}}$$

where as always $k=2m+N-1$, i.e.

$$m = \frac{k - N + 1}{2}.$$

Again, if m>0, R=V/2, then we may equivalently write $$P(x \mid \mu, m, R, N) = \frac{\Gamma\left(m + \frac{N}{2}\right)}{(2\pi)^{\frac{N}{2}} \Gamma(m)} \frac{\det(R)^{m + \frac{N-1}{2}}}{\det\left(R + \frac{1}{2}(x-\mu)(x-\mu)'\right)^{m+\frac{N}{2}}}$$

while if $T = R^{-1}$ we have $$P(x \mid \mu, m, T, N) = \frac{\Gamma\left(m + \frac{N}{2}\right)}{\Gamma(m)} \frac{\sqrt{\det\left(\frac{T}{2\pi}\right)}}{\left(1 + \frac{1}{2}(x-\mu)'T(x-\mu)\right)^{m+\frac{N}{2}}}$$

In the particular case that $V = 2rI_N$ (as is of course always the case if N=1 for some r), this simplifies to $$\therefore P(x \mid \mu, k, r, N) = \frac{\Gamma\left(m + \frac{N}{2}\right)}{(2\pi)^{\frac{N}{2}} \Gamma(m)} \frac{r^m}{\left(r + \frac{1}{2}\|x-\mu\|^2\right)^{m+\frac{N}{2}}}.$$

Importantly, the multidimensional Student may be sampled by first sampling an auxiliary variable (the Student composer) α from a Γ(m,1) distribution, then sampling x from a multidimensional Gaussian with mean μ and scale matrix αT Often we may wish to sample from a multidimensional Student which is specified not in terms of the scale matrix but in terms of the its actual covariance (say W) and the shape. We then sample α from a Γ(m,m−1) distribution followed by x from a multidimensional Gaussian with mean μ and scale matrix $\alpha W^{-1}$.

To complicate matters further, the Student distribution may also be specified in terms of a scale matrix, also denoted T, equal to $W^{-1}$; it is in fact this approach that is adopted in the description of this specific invention in section 2 below.
An additional important special case for this application is the 1-dimensional special case with m=1, r=1, μ=0, from which a random sample may be obtained by drawing a random number u from the open interval (−1,1) (Note: not (0,1)) and then calculating $$x = \frac{u\sqrt{2}}{\sqrt{(u-1)(u+1)}}.$$

1.8.7 Log-Student

In some ways similar to the log-Gaussian distribution is the log-Student distribution, given by $P(x \mid \mu, m, T, N) =$ $$\frac{\Gamma\left(m + \frac{N}{2}\right)}{\Gamma(m)} \frac{\sqrt{\det\left(\frac{T}{2\pi}\right)}}{\left(1 + \frac{1}{2}(\log(x) - \mu)'T(\log(x) - \mu)\right)^{m+\frac{N}{2}}} \left(\prod_{n=1}^{N} \frac{1}{x_n}\right).$$

One important difference from the log-Gaussian is that the log-Student always has two peaks (or modes) for each of its marginal coordinate distributions, one of which is always at zero and of unbounded height, while the log-Gaussian only has a single mode in the expected place. Sampling from the log-Student distribution simply consists of sampling from the Student distribution with the same parameters, then exponentiating each element (coordinate) of the resulting sample vector x, i.e. replacing $$\begin{pmatrix} x_1 \\ x_2 \\ \vdots \\ x_N \end{pmatrix} \text{ by } \begin{pmatrix} e^{x_1} \\ e^{x_2} \\ \vdots \\ e^{x_N} \end{pmatrix}.$$

2 Detailed Description of the Application of Bayesian Inference to the Invention As with the specification of any problem to be solved using Bayesian inference, we must first describe the problem in detail, covering the prior, the likelihood, and the hierarchy of distributions on the parameters.

2.1 Notation and Mathematical Description of the Model of the Problem

In the following sections the parameters A, m, T need to be determined by the methods described in section 2.5 below, while the parameters μ,S are simply set in such a way that the prior on the droplet size distribution described in section 2.1.4 below matches what is known in advance about the droplet size distribution as closely as possible; the preferred values of μ,S for one particular application (inhaler droplet cloud measurement) are specifically given in section 2.1.4.

2.1.1 Notational Modifications

First, the radius of a droplet, r, we will consider to be quantised; in this embodiment this is likely to be into 70 bins spaced in even increments not of r but of log(r); thus the centres of the first and last few bins are $1.0000 \times 10^{-7}$, $1.1052 \times 10^{-7}$, $1.2214 \times 10^{-7}$, $1.3499 \times 10^{-7}$, $1.4918 \times 10^{-7}$, $1.6487 \times 10^{-7}$, ..., $8.1241 \times 10^{-5}$, $8.9785 \times 10^{-5}$, $9.9227 \times 10^{-5}$ meters. The function x then simply becomes a vector of 70 elements, each of which denotes the number of droplets per cubic meter with radius in the bin centred on the corresponding quantised value of r.

Second, we are dealing with a number of sensing channels; in the preferred embodiment this is 64, composed of 8 receive channels active while LED 1 is active, another 8 receive channels active while LED 2 is active, etc, for each of the 8 LEDs and hence giving 64 measurements, each of which is a real number representing the light power received in that channel during the relevant period of interrogation of the droplet cloud. Such a vector of (e.g.) 64 real numbers constitutes the measured vector z.

2.1.2 The Prior on the Noise

For this particular instrument we believe that the noise vector n (which in the preferred embodiment is 64-dimensional) is Student distributed with shape m=2 and scale matrix some diagonal matrix T with all diagonal elements positive (i.e. T is the matrix so denoted in the penultimate paragraph of section 1.8.6 above). Note that these assumptions are subject to modification once we have fully working hardware. For the purpose of using this prior we will consider it to be decomposed by the following formula (as mentioned under sampling in section 1.8.6 above):

$$P(n) = \int P(\lambda) P(n \mid \lambda) d\lambda$$

$$= \int \frac{(m-1)^m}{\Gamma(m)} \lambda^{m-1} e^{-(m-1)\lambda} P(n \mid \lambda) d\lambda$$

$$= \int \frac{(m-1)^m}{\Gamma(m)} \lambda^{m-1} e^{-(m-1)\lambda} \sqrt{\det\left(\frac{\lambda T}{2\pi}\right)} e^{-\frac{1}{2}\lambda n'Tn} d\lambda$$

so that $\lambda$ is a $\Gamma_{m,m-1}$-distributed variable (known as the "Student composer for the noise") and $P(n|\lambda)$ is then Gaussian with zero mean and scale matrix $\lambda T$.

2.1.3 The Likelihood

Now, the function a that maps x to y is specified by the Mie scattering equations (for which see C. F. Bohren, D. R. Huffmann: Absorption and scattering of light by small particles. New York, Wiley-Interscience, 1983 chapters 1-4, the disclosure of which is incorporated herein by reference) combined with the effects of the transmission and collection optics, which result, after integration over the areas of the transmit and receive lenses, in a function a that is linear; in other words for any non-negative real numbers $\alpha_1, \alpha_2$ and any two size-concentration vectors $x_1, x_2$ we have $a(\alpha_1 x_1 + \alpha_2 x_2) = \alpha_1 a(x_1) + \alpha_2 a(x_2)$.

As a result of this the function a may be represented by multiplication by a (not usually square) matrix A, so that we then have $z = Ax + n$. In consequence of this and of section 2.1.2 the likelihood given the Student composer of the noise may then be written $$P(z|x, \lambda, A) = \sqrt{\det\left(\frac{\lambda T}{2\pi}\right)} e^{-\frac{1}{2}\lambda(Ax-z)'T(Ax-z)}$$

so that the full likelihood becomes $$P(z|x, A) = \int \frac{(m-1)^m}{\Gamma(m)} \lambda^{m-1} e^{-(m-1)\lambda} \sqrt{\det\left(\frac{\lambda T}{2\pi}\right)} e^{-\frac{1}{2}\lambda(Ax-z)'T(Ax-z)} d\lambda.$$

2.1.4 The Prior on the Size-concentration Spectrum

To fully specify the problem we must also specify what we know about the size-concentration spectrum in advance of collecting the data.

In order to do this we note that, in the settings in which the preferred embodiment is expected to be used, the fraction of the total liquid mass contained in droplets in each radius bin is expected to vary smoothly with bin number; in other words, for example, we do not expect to find that 50% of the total liquid mass is in droplets of radii between 4.47 and 4.94 μm and 40% between 3.66 and 4.04 μm but with less than 1% between 4.04 and 4.47 μm. Put another way, we expect the fraction of overall liquid volume to be distributed similarly to the blue curves in FIG. 27 and not like those of FIG. 28 below. Of course, this statement is based on the particular use expected for the preferred embodiment, and is based on the fact that liquid nebuliser devices do not usually produce highly uniform droplet radii; if instead we had an application where the curves of FIG. 28 would be expected, then we would simply change the parameters of the prior specified for the preferred embodiment below (and might then also need to change the design of the optical sensor and hence the matrix A).

We note also that the number of droplets per unit volume in any bin cannot be negative and is rather unlikely to be zero. Accordingly we choose a log-Gaussian prior for the size-concentration vector x, with parameters to be set as described below.

Just as we might change the parameters for this distribution under alternative conditions of use of the instrument, further, we might change the prior to be log-Student rather than log-Gaussian, and introduce a second Student composer for the measurand (the first one having been introduced for the noise in section 2.1.2)) which we would sample in an exactly analogous way to that (yet to be described) in which we currently sample the Student composer for the noise. For the preferred embodiment we expect to set the median number of droplets per unit volume in a bin of radius r to be proportional to $$\frac{2r^{-6}}{r^{-4}r_0^{-2} + r^{-2}r_0^{-4}}$$

where $r_0$ takes the value 2 μm and with the constant of proportionality set such that the expected total liquid volume in the droplets is $10^{-5}$ times the total volume of air in which the cloud sits. Note that these settings are dependent upon the fact that the quantisation is such that log r is uniformly spaced over the bins.

For the preferred embodiment we expect to set the scale matrix S of the log-Gaussian prior to be as indicated in FIG. 29; this achieves the smoothness seen in FIG. 27.

2.1.5 The Model Hierarchy

The model hierarchy here is relatively simple. We represent the likelihood to be decomposed as described in 2.1.3 above, which gives us the following model structure:

Specify fixed values for the parameters m,μ,S,T (of which the last two are matrices) according to the available prior knowledge and calculate the value of the matrix A from the optical geometry chosen and the Mie scattering equations (for which see Bohren and Huffmann).

$$P(x|\mu, S) = \sqrt{\det\left(\frac{S}{2\pi}\right)} \left(\prod_{n=1}^{N} \frac{1}{x_n}\right) e^{-\frac{1}{2}(\log(x)-\mu)'S(\log(x)-\mu)}$$

$$P(\lambda|m) = \frac{(m-1)^m}{\Gamma(m)} \lambda^{m-1} e^{-(m-1)\lambda}$$

$$P(z|x, \lambda, A) = \sqrt{\det\left(\frac{\lambda T}{2\pi}\right)} e^{-\frac{1}{2}\lambda(Ax-z)'T(Ax-z)}$$

These three equations (and all the work that has gone into establishing the values of the various constant numbers and matrices in them) constitute the model to be inferred once we are given the value of the observed scattering measurement vector z.

2.2 Inference Using the Model Given an Observed Scattering Vector

We now apply Bayes theorem, using the model equations of section 2.1.5, as follows.

$$P(x, \lambda | z, m, \mu, S, T) = \frac{P(x|\mu, S)P(\lambda|m)P(z|x, \lambda, T)}{\int P(x|\mu, S)P(\lambda|m)P(z|x, \lambda, T)d(x, \lambda)} =$$

$$\frac{\sqrt{\det\left(\frac{S}{2\pi}\right)}\left(\prod_{n=1}^{N}\frac{1}{x_n}\right)e^{-\frac{1}{2}(\log(x)-\mu)'S(\log(x)-\mu)}\frac{(m-1)^m}{\Gamma(m)}\lambda^{m-1}e^{-(m-1)\lambda}\sqrt{\det\left(\frac{\lambda T}{2\pi}\right)}e^{-\frac{1}{2}\lambda(Ax-z)'T(Ax-z)}}{\int \sqrt{\det\left(\frac{S}{2\pi}\right)}\left(\prod_{n=1}^{N}\frac{1}{x_n}\right)e^{-\frac{1}{2}(\log(x)-\mu)'S(\log(x)-\mu)}\frac{(m-1)^m}{\Gamma(m)}\lambda^{m-1}e^{-(m-1)\lambda}\sqrt{\det\left(\frac{\lambda T}{2\pi}\right)}e^{-\frac{1}{2}\lambda(Ax-z)'T(Ax-z)}d(x,\lambda)} =$$

$$\frac{\left(\prod_{n=1}^{N}\frac{1}{x_n}\right)e^{-\frac{1}{2}(log(x)-\mu)'S(log(x)-\mu)}\lambda^{m-1}e^{-(m-1)\lambda}e^{-\frac{1}{2}\lambda(Ax-z)'T(Ax-z)}}{\int\left(\prod_{n=1}^{N}\frac{1}{x_n}\right)e^{-\frac{1}{2}(log(x)-\mu)'S(log(x)-\mu)}\lambda^{m-1}e^{-(m-1)\lambda}e^{-\frac{1}{2}\lambda(Ax-z)'T(Ax-z)}d(x,\lambda)}$$

Thus we have $$P(x, \lambda \mid z, m, \mu, S, T) =$$

$$\frac{\lambda^{m-1}\left(\prod_{n=1}^{N}\frac{1}{x_n}\right)e^{-\frac{1}{2}(log(x)-\mu)'S(log(x)-\mu)-(m-1)\lambda-\frac{1}{2}\lambda(Ax-z)'T(Ax-z)}}{\int\lambda^{m-1}\left(\prod_{n=1}^{N}\frac{1}{x_n}\right)e^{-\frac{1}{2}(log(x)-\mu)'S(log(x)-\mu)-(m-1)\lambda-\frac{1}{2}\lambda(Ax-z)'T(Ax-z)}d(x,\lambda)}$$

Although the end user is not interested in knowing the value of $\lambda$, we have treated $\lambda$ here as though the end user wants to know its value also. It so happens that it is easier to do that, and then throw away the information we have found on $\lambda$, than to take the more obvious route.

At this point our appropriate desire to solve the problem analytically comes to a stop, as the integral in the denominator is believed to be intractable. Fortunately, the solution may be obtained due to the availability of MCMC methods.

2.3 The MCMC Sampling Scheme

We therefore desire to obtain samples from the above distribution on $(x,\lambda)$ using an MCMC scheme. Here are the details of that scheme.

2.3.1 Top Level Plan

The top level plan is to use simulated annealing (section 1.5.6 above) starting from $$P_0(x, \lambda \mid m, S, \mu) = \frac{(m-1)^m}{\Gamma(m)}\lambda^{m-1}e^{-(m-1)\lambda}\sqrt{\det\left(\frac{S}{2\pi}\right)}\left(\prod_{n=1}^{N}\frac{1}{x_n}\right)e^{-\frac{1}{2}(log(x)-\mu)'S(log(x)-\mu)}$$

and concluding at $$P_1(x, \lambda \mid z, m, \mu, S, T) =$$

$$Z\lambda^{m-1}\left(\prod_{n=1}^{N}\frac{1}{x_n}\right)e^{-\frac{1}{2}(log(x)-\mu)'S(log(x)-\mu)-(m-1)\lambda-\frac{1}{2}\lambda(Ax-z)'T(Ax-z)}$$

where $$Z = \frac{1}{\int\lambda^{m-1}\left(\prod_{n=1}^{N}\frac{1}{x_n}\right)e^{-\frac{1}{2}(log(x)-\mu)'S(log(x)-\mu)-(m-1)\lambda-\frac{1}{2}\lambda(Ax-z)'T(Ax-z)}d(x,\lambda)}$$

is an unknown constant, and using $$\kappa_k = 10^{-2\frac{K-k}{K}}$$

for $0 \leq k \leq K = 30000$. In other words we will start by drawing a sample of $(x,\lambda)$ from $P_0$ (according to the methods detailed in 1.8.3 and 1.8.4 above), draw each subsequent sample forming a sequence of 30 thousand samples according to moves (yet to be specified in section 2.3.2 below) that satisfy detailed balance for the $P_{\kappa_k}$ defined in 1.5.6 from $P_0$ and $P_1$, then draw a further number (in this embodiment 50 thousand) of samples using MCMC moves that satisfy detailed balance for $P_1$. Finally we will take a subset of the last 50000 samples (as many, up to 50000, as the end user would like) evenly spaced through the sequence of samples, and compute any derived properties (e.g. mode, mean droplet radius, total fluid volume in droplets, etc) by computing the desired property (say $h(x)$) for each of the samples $x_n$ of $x$, and then returning the mean $$\frac{1}{N}\sum_{n=1}^{N}h(x_n)$$

of the said properties $h(x_n)$ and any desired quantiles or histogram of the computed property values.

2.3.2 Second Level Plan

At the second level we have to provide moves (i.e. methods of drawing new samples of $(x,\lambda)$ that satisfy detailed balance with respect to any $P_{\kappa_k}$.

We do this using modified Gibbs sampling (section 1.5.4 above). We combine moves that resample $\lambda$ (section 2.3.3) with moves that resample $x$ (section 2.3.4) palindromically (section 1.5.2), using alternating palindromes $\lambda,x,\lambda$ and $x,\lambda,x$, thus effectively simply alternating moves that resample $\lambda$ with moves that resample $x$. Note, however, that if a second Student composer were introduced to convert the prior on $x$ from a log-Gaussian to a log-Student distribution, then we would resample both Student composers in one operation alternating with resampling $x$. If further complications were added to the model, we would no longer simply be doing alternating moves, but the palindromic structure (or the alternative random structure—section 1.5.2) would then remain in a more obvious form. Note also that an alternative embodiment might use random rather than palindromic combination.

2.3.3 Bottom Level Plan—Resampling $\lambda$

For the component move in 2 we use an exact Gibbs sampling move, which is possible since the distribution of $\lambda \mid \kappa, z, m, \mu, S, T$ turns out to be Gamma thanks to the designed conjugacy (section 1.6.1 above), so the prior art random sampling schemes for Gamma distributions (section 1.8.4 above) can be used.

2.3.4 Bottom Level Plan—Resampling x—Preferred Embodiment

To resample x we use Metropolis-Hastings moves (section 1.5.5 above). This leaves the proposal distribution $g(x \mid x_n, \kappa, \lambda, z, m, \mu, S, T)$ to be specified.

2.3.4.1 Currently Preferred Proposal Distribution

Many proposal distributions are possible. The precise one that works best is unknown in the sense that there is no way of proving that you have picked the one that gives fastest running. Moreover the best of the ones we have found varies with the precise details of the optical configuration used. Accordingly we note that for the preferred optical configuration the best found proposal distribution is log Student with dimensionality N=70, median $x_n$, shape m=2, and scale matrix (as in the T defined in section 1.8.7) given by $$\frac{\lambda\sqrt{\kappa}}{\varepsilon^2(m-1)}S$$

with $\epsilon=10^{-2}$, but we also note the following alternative possibilities for the proposal distribution.

2.3.4.2 Alternative Possible Proposal Distributions

Clearly log-Student with a variety of other parameter settings is possible. In particular using a scale matrix that is a different multiple of S, or a multiple of the matrix square root of S times the square root of its leading diagonal element, or a multiple of the identity times the leading diagonal element of S are all sensible things to consider. Likewise log-Gaussian with any of the above scale matrices would be reasonable to consider. Further, using a scale matrix that is a multiple of the Hessian of the posterior distribution of $x|\kappa,\lambda,z,m,\mu,S,T$ with respect to x would be a sensible alternative to try.

2.3.5 Bottom Level Plan—Resampling x—Other Possibilities

It would also be possible to resample $x|\kappa,\lambda,z,m,\mu,S,T$ using Gibbs sampling over the coordinates of x, as well as many many other (and mostly less satisfactory) possibilities.

2.4 Typical Output of the Inference Process

Figure 19:
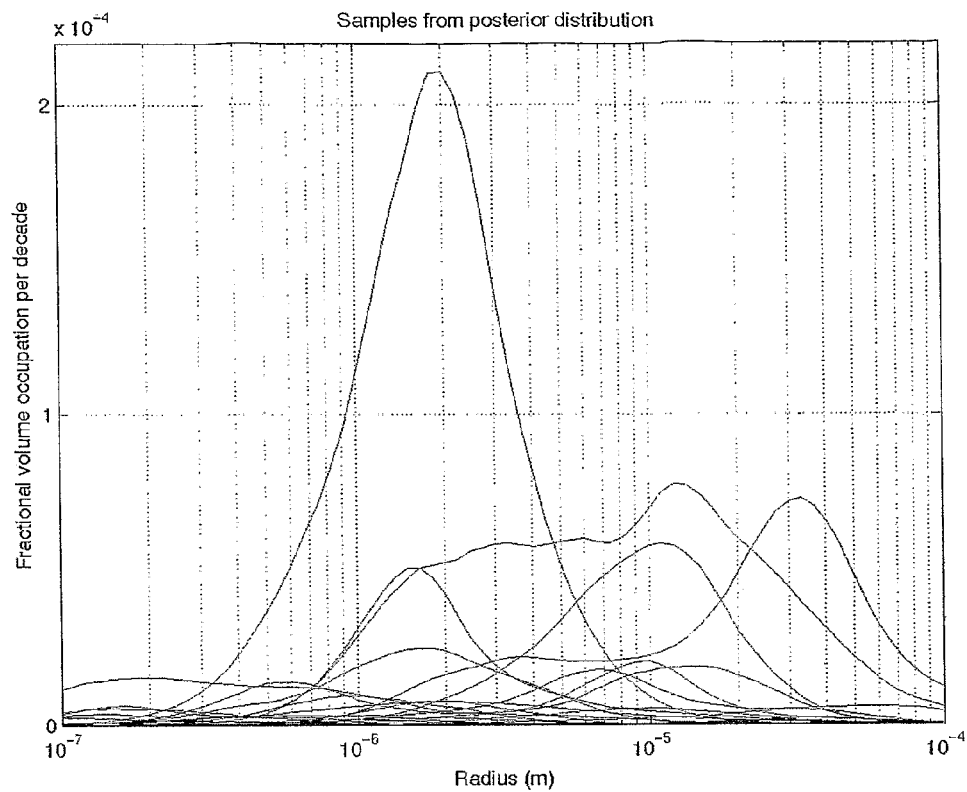
FIGS. 19 and 20 are typical samples from the prior on the size-concentration vector.
Figure 20:
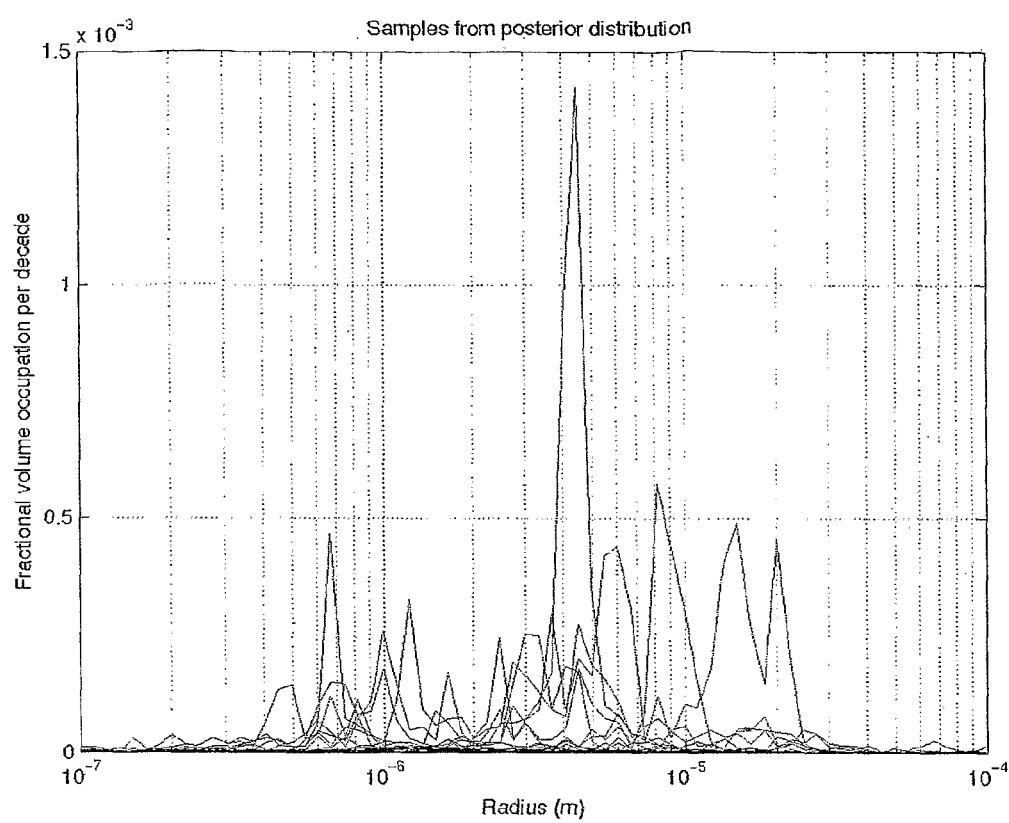
Figure 21:
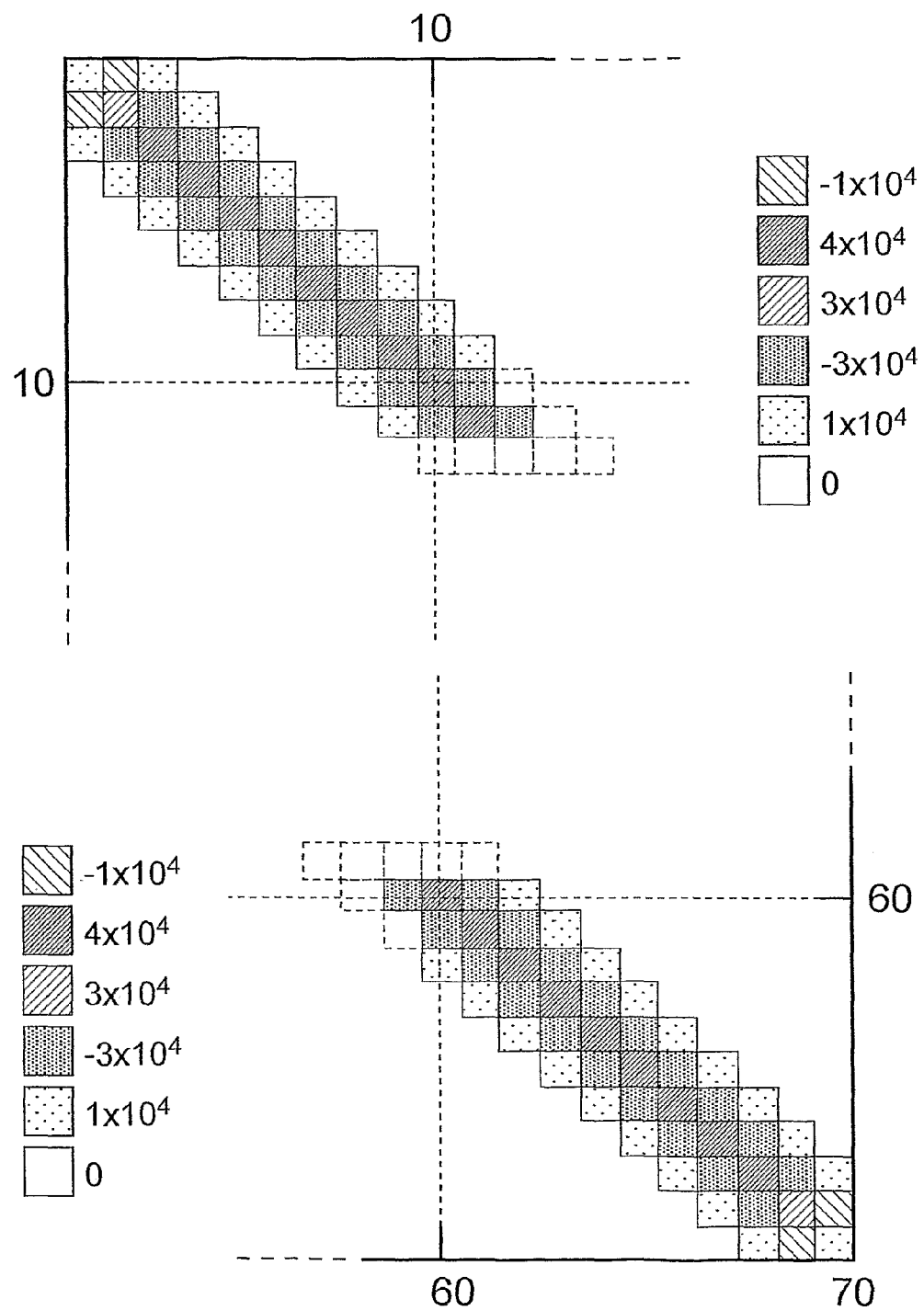
FIG. 21 shows a scale matrix of the log-Gaussian prior for the size-concentration vector in the droplet size determination.

We have already shown in FIG. 19 what typical samples from the prior distribution on x look like. It is however more useful to display them with a logarithmic vertical scale, as shown now in 30.

Now, suppose we consider a possible true value of x, shown as line A in FIG. 23, and collect a typical measured value of z, either using the model in section 2.1.5 or by using a real sensor. We then apply Bayesian inference as described and obtain a number of samples (shown as lines B in FIG. 23) of what the true value of x can now be believed to be in the light of the prior and of the observed value z. As can be seen the blue curves bunch tightly together over most of the range of droplet radius of interest. The curves C give us the 90% confidence (or credible) intervals for the marginal values $x(r)|z$; in other words for any single fixed value of r, there is, in the light of the observed data z, a probability of 0.9 that the true value of $x(r)$ lies between the two magenta curves.

FIG. 23 shows that given this sensor configuration and this true value of x, the number of droplets around 1 μm radius can be determined to a much greater proportional accuracy than can the number of droplets of around 10 μm radius; this is in part due to the properties of the optical configuration, and in part due to the fact that there just are (in truth) fewer droplets of 10 μm radius than there are of 1 μm radius, and hence the proportional accuracy is bound to be lower.

2.5 Determining the Values of the Input Parameters A,m,T

This section describes the methods by which the input parameters A,m,T are determined.

2.5.1 Determining A

To determine A, we apply the Mie scattering equations from Bohren and Huffman to the geometry of the hardware in question to establish, for unit quantity of spherical droplets distributed uniformly in log-radius within each given size bin, the difference between the value of the signal obtained in each channel with those droplets alone present and the value of the signal obtained at each detector with no droplets present (and no noise). Each such calculation gives us one element of the matrix A, which has as many rows as there are size bins, and as many columns as there are detection channels (i.e. 64 in the preferred embodiment).

Thus this step is entirely conventional; while it is hardly simple, it is entirely described within the first four chapters of Bohren and Huffman.

2.5.2 Determining the Parameters m,T

In the absence of any data from the hardware, our preferred embodiment would set the values of m and T as discussed in the first paragraph of section 2.1.2 above. However, this can be improved on given data from the real hardware, as follows.

In order (once and for all for each design of optical hardware) to determine the parameters m and T, we first collect samples of noise from the optical hardware in question, by collecting a large number of data vectors $z_1, z_2, \ldots, z_K$ in the absence of any droplets, using exactly the same collection method and collection time as we would for collecting a scattering vector for determining droplet size distribution.

Having collected that dataset, we set a Wishart prior (section 1.8.5) on the parameter T (with shape, say, of 1, and scale matrix the identity times the expected squared noise voltage amplitude), and (for example) a broad Gamma prior (section 1.8.4) or a log-Gaussian prior (section 1.8.3) on m, ensuring we have high prior density at values of in from 1.5 to (say) 20; we set the likelihood as defined in section 2.1.2 for each of the $z_k$; and we use MCMC (specifically Gibbs sampling (section 1.5.3) using the axes T|m and m|T) to infer a set of joint posterior samples on m and T. We then use the average of the posterior samples of m as the input value of the parameter m, and the average of the posterior samples of T as the input value of the parameter T.

The invention claimed is:

1. A photometric device which comprises:
   an array of radiation sources that are spaced apart from one another, and which are operable to generate radiation that differs from that generated by at least one other radiation source in the array, and
   a lens arrangement for directing radiation from the radiation sources to a region of space, and at least one radiation detector for receiving radiation from the region of space;
   the device further comprising signal processing means for determining a size distribution of a sample of particles in said region of space on the basis of scattering data of the particles, the signal processing means operable to:
   (a) determine a scattering vector z for scattering of radiation of a number of different wavelengths and polarisation states by the sample of particles at a number of different scattering angles; and
   (b) apply Bayesian inference to the scattering vector to determine the posterior probability distribution of the mean over a period of time of the particle size distribution from prior information regarding the likely particle size distribution and the Mie scattering equations for determining the scattering vector z from the size distribution.

2. A device as claimed in claim 1, wherein each radiation source is associated with a primary objective lens for collimating radiation from the source.

3. A device as claimed in claim 2, which includes a common source objective lens for directing the collimated radiation from the radiation sources to the region of space.

4. A device as claimed in claim 3, wherein the common source objective lens is divided into a plurality of parts so that rays from different radiation sources will pass through different parts of the common source objective lens.

5. A device as claimed in claim 4, wherein the common source objective lens has a hole therethrough located between the parts thereof through which radiation from the radiation sources passes, in order to prevent or reduce cross-talk between radiation from different radiation sources.

6. A device as claimed in claim 1, which includes a polarizing or spectral filter associated with at least some of the radiation sources to alter an optical property of the radiation generated by the radiation sources.

7. A device as claimed in claim 1, which includes a common detector objective lens for focusing radiation that has passed through the region of space to form a plurality of rays that are generally parallel and directed toward the radiation detectors.

8. A device as claimed in claim 7, wherein the common detector objective lens is divided into a plurality of parts such that the rays for different detectors pass through the different parts of the common detector objective lens.

9. A device as claimed in claim 8, wherein the common detector objective lens has a hole therethrough located between the parts thereof through which radiation from the region of space passes to the detectors, in order to prevent or reduce cross-talk between radiation passing to different radiation detectors.

10. A device as claimed in claim 1, wherein each radiation detector is associated with an objective lens for focusing the rays that are generally parallel onto the radiation detector.

11. A device as claimed in claim 1, which includes a sample holder for holding a sample to be investigated in the region of space.

12. A device as claimed in claim 6, wherein the filter associated with at least some of the radiation sources comprises a polarizer, and the device includes a polarizer associated with at least some of the radiation detectors.

13. A device as claimed in claim 1, which includes a time division multiplexer for time division multiplexing the radiation sources so that, in operation, a sample will be illuminated by radiation from only one of the radiation sources at any time.

14. A device as claimed in claim 1, which includes a processor for processing signals generated by the at least one radiation detector, so that radiation that has been scattered by the sample can be detected in addition to or instead of radiation that has passed through the region of space.

15. A device as claimed in claim 14, wherein the processor is operable to process signals generated by the at least one radiation detector for radiation generated by each radiation source.

16. A device as claimed in claim 1, wherein the at least one radiation detector is located on the same side of an element to be illuminated as the array of radiation sources in order to detect radiation that is backscattered by the element to be illuminated.

17. A device as claimed in claim 14, wherein the processor is operable to process signals generated by an array of radiation detectors after radiation from the radiation sources has been modulated in power in order to enable the device to detect time delayed fluorescence.

18. A device as clamed in claim 1, which includes an optical waveguide that extends from the region of space to a volume in which a sample to be investigated is located.

19. A device as claimed in claim 18, wherein the optical waveguide is an optical fibre.

20. A method of conducting a photometric examination of a sample of particles, comprising:
locating the sample of particles in a region of space in a photometric device, comprising:
an array of radiation sources spaced apart from one another, wherein the radiation sources generate radiation that differs from that generated by at least one other radiation source in the array,
(ii) a lens arrangement for directing radiation from the radiation sources to the region of space, and
(iii) at least one radiation detector for receiving radiation from the region of space;
illuminating the sample of particles by means of the photometric device; and processing signals obtained from the radiation detectors detectors to:
(a) determine a scattering vector z for scattering of radiation of a number of different wavelengths and polarisation states by the sample of particles at a number of different scattering angles; and
(b) apply Bayesian inference to the scattering vector to determine the posterior probability distribution of the mean over a period of time of the particle size distribution from prior information regarding the likely particle size distribution and the Mie scattering equations for determining the scattering vector z from the size distribution.

* * * * *